United States Patent
Ross et al.

(10) Patent No.: US 11,793,179 B2
(45) Date of Patent: Oct. 24, 2023

(54) LIVESTOCK ANIMALS WITH IMPROVED GROWTH PERFORMANCE

(71) Applicant: Iowa State University Research Foundation, Inc., Ames, IA (US)

(72) Inventors: Jason Wayne Ross, Ames, IA (US); Ronald Blythe Schultz, Ames, IA (US); Nicholas Kurt Gabler, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 198 days.

(21) Appl. No.: 17/248,071

(22) Filed: Jan. 7, 2021

(65) Prior Publication Data
US 2021/0204529 A1 Jul. 8, 2021

Related U.S. Application Data

(60) Provisional application No. 62/957,861, filed on Jan. 7, 2020.

(51) Int. Cl.
*A01K 67/027* (2006.01)
*C12N 15/90* (2006.01)

(52) U.S. Cl.
CPC ........ *A01K 67/0276* (2013.01); *C12N 15/907* (2013.01); *A01K 2217/075* (2013.01); *A01K 2217/203* (2013.01); *A01K 2227/108* (2013.01); *A01K 2267/02* (2013.01); *C12N 2310/20* (2017.05); *C12N 2800/80* (2013.01)

(58) Field of Classification Search
CPC .......... A01K 67/0276; A01K 2217/075; A01K 2217/203; A01K 2227/108; A01K 2267/02; C12N 15/907; C12N 2310/20; C12N 2800/80
See application file for complete search history.

(56) References Cited

U.S. PATENT DOCUMENTS

| | | | |
|---|---|---|---|
| 4,599,229 A * | 7/1986 | Maccecchini | A61P 3/00 424/809 |
| 5,436,155 A | 7/1995 | Bell et al. | |
| 5,723,299 A | 3/1998 | Bell et al. | |
| 2002/0016298 A1* | 2/2002 | Hay | C07K 5/06156 514/12.3 |

OTHER PUBLICATIONS

Wang et al. Efficient Generation of Myostatin Mutations in Pigs Using the CRISPR/Cas9 System. Scientific Reports. 2015; 5: 16623. (Year: 2015).*

(Continued)

*Primary Examiner* — Arthur S Leonard
*Assistant Examiner* — Jianjian Zhu
(74) *Attorney, Agent, or Firm* — McKee, Voorhees & Sease, PLC

(57) ABSTRACT

Livestock animals and progeny thereof comprising at least one edited chromosomal sequence that alters expression or activity of a somatostatin receptor (SSTR) protein are provided. Livestock animal cells that contain such edited chromosomal sequences are also provided. The livestock animals have improved growth performance and weight gain. Methods for producing livestock animals with increased growth performance are also provided.

20 Claims, 7 Drawing Sheets

Specification includes a Sequence Listing.

(56) References Cited

OTHER PUBLICATIONS

Leuchs et al. Inactivation and Inducible Oncogenic Mutation of p53 in Gene Targeted Pigs. PLoS ONE. 2012; 7(10): e43323. (Year: 2012).*

Ben-Shlomo et al. Pituitary somatostatin receptor signaling. Trends in Endocrinology and Metabolism. 2010; 21(3): 123-133. (Year: 2010).*

Ben-Shlomo et al., "Constitutive Somatostatin Receptor Subtype 2 Activity Attenuates GH Synthesis", Endocrinology, vol. 154, No. 7, pp. 2399-2409, Jul. 2013.

Brazeau, Paul, "Somatostatin: A Peptide with Unexpected Physiologic Activities", The American Journal of Medicine, vol. 81, (Suppl 6B), pp. 8-13, Dec. 12, 1986.

Buonomo et al., "Effects of Somatostatin Immunoneutralization on Growth and Endocrine Parameters in Chickens", Domestic Animal Endocrinology, vol. 4, No. 3, pp. 191-200, 1987.

Gahete et al., "Somatostatin and its receptors from fish to mammals", Ann N.Y. Acad Sci., ISSN 0077-8923, pp. 13-52, 2010.

Patel, Yogesh, "Somatostatin and Its Receptor Family", Frontiers in Neuroendocrinology, vol. 20, pp. 157-198, 1999.

Patel et al., "Mini Review The Somatostain Receptor Family", Life Sciences, vol. 57, No. 13, pp. 1249-1265, 1995.

Spencer et al., "A Novel Approach to Growth Promotion Using Auto-Immunisation Against Somatostatin. I. Effects on Growth and Hormone Levels in Lambs", Livestock Production Science, vol. 10, pp. 25-37, 1983.

Spencer et al., "The Effect of Immunization Against Somatostatin on Growth Rates and Growth Hormone Secretion in the Chicken", Comp. Biochem. Physiol., vol. 85A, No. 3, pp. 553-556, 1986.

Wang et al., "Alterations in glucose homeostasis in SSTR1 gene-ablated mice", Molecular and Cellular Endocrinology, vol. 247, pp. 82-90, 2006.

Zheng et al., "Somatostatin Receptor Subtype 2 Knockout Mice Are Refractory to Growth Hormone-Negative Feedback on Arcuate Neurons", Molecular Endocrinology, vol. 11, No. 11, pp. 1709-1717, 1997.

* cited by examiner

```
TTGGAACTAGCCTGGGACTGTCAGGCAGCCATGGATATGGCGTATGAGCTACTCAACGGGAGCCAGCCGTGGCTTTCCTCTCCATTC  (SEQ ID NO 6)
-------------------------------------TGGCGTATGAGCTACTCAAC--------------------------------  (SEQ ID NO 5)
TTGGAACTAGCCTGGGACTGTCAGGCAGCCATGGATATGGCGTATGAGCTA---AACGGGAGCCAGCCGTGGCTTTCCTCTCCATTC  (SEQ ID NO 7)
TTGGAACTAGCCTGGGACTGTCAGGCAGCCATGGATATGGCGTATGAGCTACTC-ACGGGAGCCAGCCGTGGCTTTCCTCTCCATTC  (SEQ ID NO 8)
TTGGAACTAGCCTGGGACTGTCAGGCAGCCATGGATATGGCGTATGAGCTA---CACGGGAGCCAGCCGTGGCTTTCCTCTCCATTC  (SEQ ID NO 9)
TTGGAACTAGCCTGGGACTGTCAGGCAGCCATGGATATGGCGTATGAGCTACTC-ACGGGAGCCAGCCGTGGCTTTCCTCTCCATTC  (SEQ ID NO 8)
TTGGAACTAGCCTGGGACTGTCAGGCAGCCATGGATATGGCGTATGAGCTACTC-ACGGGAGCCAGCCGTGGCTTTCCTCTCCATTC  (SEQ ID NO 8)
TTGGAACTAGCCTGGGACTGTCAGGCAGCCATGGATATGGCGTATGAGCTACTC-ACGGGAGCCAGCCGTGGCTTTCCTCTCCATTC  (SEQ ID NO 8)
TTGGAACTAGCCTGGGACTGTCAGGCAGCCATGGATATGGCGTATGAGCTA---AACGGGAGCCAGCCGTGGCTTTCCTCTCCATTC  (SEQ ID NO 7)
TTGGAACTAGCCTGGGACTGTCAGGCAGCCATGGATATGGCGTATGAGCTACTC-ACGGGAGCCAGCCGTGGCTTTCCTCTCCATTC  (SEQ ID NO 8)
TTGGAACTAGCCTGGGACTGTCAGGCAGCCATGGATATGGCGTATGAGCTA---AACGGGAGCCAGCCGTGGCTTTCCTCTCCATTC  (SEQ ID NO 7)
TTGGAACTAGCCTGGGACTGTCAGGCAGCCATGGATATGGCGTATGAGCTACTC-ACGGGAGCCAGCCGTGGCTTTCCTCTCCATTC  (SEQ ID NO 8)
TTGGAACTAGCCTGGGACTGTCAGGCAGCCATGGATATGGCGTATGAGCTA---AACGGGAGCCAGCCGTGGCTTTCCTCTCCATTC  (SEQ ID NO 7)
```

FIG. 1

```
TTGGAACTAGCCTGGGACTGTCAGGCAGCCAGGCAGCCATGGATATGGCGTATGAGCTACTCAACGGGAGCCAGCCGTGGCTTTCCTCTCCATTC  (SEQ ID NO:6)
----------------------------------------TGGCGTATGAGCTACTCAAC-----------------------------------  (SEQ ID NO:5)
TTGGAACTAGCCTGGGACTGTCAGGCAGCCAGGCAGCCATGGATATGGCGTATGAGCTA----AACGGGAGCCAGCCGTGGCTTTCCTCTCCATTC  (SEQ ID NO:7)
TTGGAACTAGCCTGGGACTGTCAGGCAGCCAGGCAGCCATGGATATGGCGTATGAGCTA----AACGGGAGCCAGCCGTGGCTTTCCTCTCCATTC  (SEQ ID NO:7)
TTGGAACTAGCCTGGGACTGTCAGGCAGCCAGGCAGCCATGGATATGGCGTATGAGCTACTC-ACGGGAGCCAGCCGTGGCTTTCCTCTCCATTC  (SEQ ID NO:8)
TTGGAACTAGCCTGGGACTGTCAGGCAGCCAGGCAGCCATGGATATGGCGTATGAGCTACTC-ACGGGAGCCAGCCGTGGCTTTCCTCTCCATTC  (SEQ ID NO:8)
TTGGAACTAGCCTGGGACTGTCAGGCAGCCAGGCAGCCATGGATATGGCGTATGAGCTA----CACGGGAGCCAGCCGTGGTTTCCTCTCCATTC  (SEQ ID NO:10)
TTGGAACTAGCCTGGGACTGTCAGGCAGCCAGGCAGCCATGGATATGGCGTATGAGCTACTC-ACGGGAGCCAGCCGTGGCTTTCCTCTCCATTC  (SEQ ID NO:8)
TTGGAACTAGCCTGGGACTGTCACGCAGCCAGGCAGCCATGGATATGGCGTATGAGCTA----AACGGAGCCAGCCGTGGCTTTCCTCTCCATTC  (SEQ ID NO:7)
TTGGAACTAGCCTGGGACTGTCAGGCAGCCAGGCAGCCATGGATATGGCGTATGAGAGATA--AACGGGAGCCAGCCGTGGCTTTCCTCTCCATTC  (SEQ ID NO:11)
TTGGAACTAGCCTGGGACTGTCAGGCAGCCAGGCAGCCATGGATATGGCGTATGAGCTA----AACGGGAGCCAGCCGTGGCTTTCCTCTCCATTC  (SEQ ID NO:7)
TTGGAACTAGCCTGGGACTGTCAGGCAGCCAGGCAGCCATGGATATGGCGTATGAGCTACTC-ACGGGAGCCAGCCGTGGCTTTCCTCTCCATTC  (SEQ ID NO:8)
```

FIG. 2

MDMAYELLNGSQPWLSSPFDLNGSVATANSSNQTEPYYDLTSNAVLTFIYFVVCIIGLCGNTLVIYVILRYA
KMKTITNIYILNLAIADELFMLGLPFLAMQVALVHWPFGKAICRVVMTVDGINQFTSIFCLTVMSIDRYLAVV
HPIKSAKWRRPRTAKMINVAVWGVSLLVILPIMIYAGLRSNQWGRSSCTINWPGESGAWYTGFIIYAFILGF
LVPLTIICLCYLFIIIKVKSSGIRVGSSKRKKSEKKVTRMVSIVVAVFIFCWLPFYIFNVSSVSVAISPTPALKG
MFDFVVVLTYANSCANPILYAFLSDNFKKSFQNVLCLVK

*FIG. 3A*

MDMAYELLTGASRGFPLHSTSMAPWQQPTVQTRRSHTMT

*FIG. 3B*

MDMAYELNGSQPWLSSPFDLNGSVATANSSNQTEPYYDLTSNAVLTFIYFVVCIIGLCGNTLVIYVILRYAK
MKTITNIYILNLAIADELFMLGLPFLAMQVALVHWPFGKAICRVVMTVDGINQFTSIFCLTVMSIDRYLAVVH
PIKSAKWRRPRTAKMINVAVWGVSLLVILPIMIYAGLRSNQWGRSSCTINWPGESGAWYTGFIIYAFILGFL
VPLTIICLCYLFIIIKVKSSGIRVGSSKRKKSEKKVTRMVSIVVAVFIFCWLPFYIFNVSSVSVAISPTPALKGM
FDFVVVLTYANSCANPILYAFLSDNFKKSFQNVLCLVK

```
                         SEQUENCE LISTING

<160> NUMBER OF SEQ ID NOS: 14

<210> SEQ ID NO 1
<211> LENGTH: 1110
<212> TYPE: DNA
<213> ORGANISM: Sus scrofa

<400> SEQUENCE: 1
atggatatgg cgtatgagct actcaacggg agccagccgt ggctttcctc tccattcgac      60
ctcaatggct ccgtggcaac agccaacagt tcaaaccaga cggagccata ctatgacctg     120
accagcaatg cagtcctcac gttcatatat tttgtggtct gcatcattgg cctgtgcggc     180
aacacgcttg tcatttacgt catcctccgc tacgccaaga tgaagacaat caccaacatc     240
tacatcctca acctggccat tgccgatgag ctcttcatgc tgggcctgcc cttcctggcc     300
atgcaggtgg ctctggtcca ctggcccttt ggcaaggcca tctgccgggt ggtcatgact     360
gtggatggca tcaatcagtt caccagcatt ttctgcttga ccgtcatgag cattgaccgg     420
tacctggctg tggtccaccc catcaagtcg gccaagtgga ggagaccccg gacagccaag     480
atgatcaatg tggccgtgtg gggcgtctct ctgctggtca tcttgcccat catgatatat     540
gccgggcttc gaagcaacca gtgggggaga agcagctgca ccatcaactg gccaggcgag     600
tcgggggcat ggtacacggg gttcattatc tacgccttca tcctgggggtt cctggtgccc     660 ctcaccatca tctgtctttg ctacctgttc attatcatca aggtgaagtc ctccggaatc     720
cgagtgggtt cctccaagag gaaaaagtct gagaagaagg tcacccggat ggtgtccatt     780
gtggtggccg tcttcatttt ctgctggctc cccttctaca tcttcaatgt ctcttcggtc     840
tctgtggcca tcagtcccac cccagccctt aaaggcatgt ttgactttgt ggtggtcctc     900
acctatgcta cagctgtgc caaccctatc ctctatgcct tcttgtccga caacttcaag     960
aagagcttcc agaatgtcct ctgcttggtc aaggtgagcg gcacagatga tgggaacgg    1020 agtgacagta agcaggacaa atcgcggctg aatgagacca cggagaccca gaggaccctc    1080
ctcaatggag acctccagac cagtatctga                                     1110

<210> SEQ ID NO 2
<211> LENGTH: 369
<212> TYPE: PRT
<213> ORGANISM: Sus scrofa

<400> SEQUENCE: 2

Met Asp Met Ala Tyr Glu Leu Leu Asn Gly Ser Gln Pro Trp Leu Ser
1               5                   10                  15
```

```
Ser Pro Phe Asp Leu Asn Gly Ser Val Ala Thr Ala Asn Ser Ser Asn
             20                  25                  30

Gln Thr Glu Pro Tyr Tyr Asp Leu Thr Ser Asn Ala Val Leu Thr Phe
         35                  40                  45

Ile Tyr Phe Val Val Cys Ile Ile Gly Leu Cys Gly Asn Thr Leu Val
 50                  55                  60

Ile Tyr Val Ile Leu Arg Tyr Ala Lys Met Lys Thr Ile Thr Asn Ile
 65                  70                  75                  80

Tyr Ile Leu Asn Leu Ala Ile Ala Asp Glu Leu Phe Met Leu Gly Leu
             85                  90                  95

Pro Phe Leu Ala Met Gln Val Ala Leu Val His Trp Pro Phe Gly Lys
            100                 105                 110

Ala Ile Cys Arg Val Val Met Thr Val Asp Gly Ile Asn Gln Phe Thr
            115                 120                 125

Ser Ile Phe Cys Leu Thr Val Met Ser Ile Asp Arg Tyr Leu Ala Val
        130                 135                 140

Val His Pro Ile Lys Ser Ala Lys Trp Arg Arg Pro Arg Thr Ala Lys
145                 150                 155                 160

Met Ile Asn Val Ala Val Trp Gly Val Ser Leu Leu Val Ile Leu Pro
                165                 170                 175

Ile Met Ile Tyr Ala Gly Leu Arg Ser Asn Gln Trp Gly Arg Ser Ser
            180                 185                 190

Cys Thr Ile Asn Trp Pro Gly Glu Ser Gly Ala Trp Tyr Thr Gly Phe
        195                 200                 205

Ile Ile Tyr Ala Phe Ile Leu Gly Phe Leu Val Pro Leu Thr Ile Ile
    210                 215                 220

Cys Leu Cys Tyr Leu Phe Ile Ile Lys Val Lys Ser Ser Gly Ile
225                 230                 235                 240

Arg Val Gly Ser Ser Lys Arg Lys Ser Glu Lys Lys Val Thr Arg
                245                 250                 255

Met Val Ser Ile Val Val Ala Val Phe Ile Phe Cys Trp Leu Pro Phe
            260                 265                 270

Tyr Ile Phe Asn Val Ser Ser Val Ser Val Ala Ile Ser Pro Thr Pro
        275                 280                 285

Ala Leu Lys Gly Met Phe Asp Phe Val Val Val Leu Thr Tyr Ala Asn
    290                 295                 300

Ser Cys Ala Asn Pro Ile Leu Tyr Ala Phe Leu Ser Asp Asn Phe Lys
305                 310                 315                 320

Lys Ser Phe Gln Asn Val Leu Cys Leu Val Lys Val Ser Gly Thr Asp
                325                 330                 335

Asp Gly Glu Arg Ser Asp Ser Lys Gln Asp Lys Ser Arg Leu Asn Glu
            340                 345                 350

Thr Thr Glu Thr Gln Arg Thr Leu Leu Asn Gly Asp Leu Gln Thr Ser
        355                 360                 365

Ile

<210> SEQ ID NO 3
<211> LENGTH: 1107
<212> TYPE: DNA
<213> ORGANISM: Artificial Sequence
<220> FEATURE:
<223> OTHER INFORMATION: Modified Sus scrofa sequence

<400> SEQUENCE: 3
atggatatgg cgtatgagct aaacgggagc cagccgtggc tttcctctcc attcgacctc      60
```

```
aatggctccg tggcaacagc caacagttca aaccagacgg agccatacta tgacctgacc    120
agcaatgcag tcctcacgtt catatatttt gtggtctgca tcattggcct gtgcggcaac    180
acgcttgtca tttacgtcat cctccgctac gccaagatga agacaatcac caacatctac    240
atcctcaacc tggccattgc cgatgagctc ttcatgctgg gcctgccctt cctggccatg    300
caggtggctc tggtccactg gcccttggc aaggccatct gccgggtggt catgactgtg     360
gatggcatca atcagttcac cagcattttc tgcttgaccg tcatgagcat tgaccggtac    420
ctggctgtgg tccaccccat caagtcggcc aagtggagga ccccggac agccaagatg      480 atcaatgtgg ccgtgtgggg cgtctctctg ctggtcatct gcccatcat gatatatgcc     540 gggcttcgaa gcaaccagtg ggggagaagc agctgcacca tcaactggcc aggcgagtcg    600
ggggcatggt acacggggtt cattatctac gccttcatcc tggggttcct ggtgcccctc    660
accatcatct gtctttgcta cctgttcatt atcatcaagg tgaagtcctc cggaatccga    720
gtgggttcct ccaagaggaa aaagtctgag aagaaggtca cccggatggt gtccattgtg    780
gtggccgtct cattttctg ctggctcccc ttctacatct tcaatgtctc ttcggtctct     840
gtggccatca gtcccacccc agcccttaaa ggcatgtttg actttgtggt ggtcctcacc    900
tatgctaaca gctgtgccaa ccctatcctc tatgccttct tgtccgacaa cttcaagaag    960
agcttccaga atgtcctctg cttggtcaag gtgagcggca cagatgatgg ggaacggagt   1020
gacagtaagc aggacaaatc gcggctgaat gagaccacgg agacccagag gaccctcctc   1080
aatggagacc tccagaccag tatctga                                        1107
```

<210> SEQ ID NO 4
<211> LENGTH: 1109
<212> TYPE: DNA
<213> ORGANISM: Artificial Sequence
<220> FEATURE:
<223> OTHER INFORMATION: Modified Sus scrofa sequence

<400> SEQUENCE: 4

```
atggatatgg cgtatgagct actcacggga gccagccgtg gctttcctct ccattcgacc     60
tcaatggctc cgtggcaaca gccaacagtt caaaccagac ggagccatac tatgacctga   120
ccagcaatgc agtcctcacg ttcatatatt ttgtggtctg catcattggc ctgtgcggca   180
acacgcttgt catttacgtc atcctccgct acgccaagat gaagacaatc accaacatct   240
acatcctcaa cctggccatt gccgatgagc tcttcatgct gggcctgccc ttcctggcca   300
tgcaggtggc tctggtccac tggcccttg gcaaggccat ctgccgggtg gtcatgactg    360
tggatggcat caatcagttc accagcattt tctgcttgac cgtcatgagc attgaccggt   420
acctggctgt ggtccacccc atcaagtcgg ccaagtggag gaccccgg acagccaaga     480 tgatcaatgt ggccgtgtgg ggcgtctctc tgctggtcat cttgcccatc atgatatatg   540
ccgggcttcg aagcaaccag tgggggagaa gcagctgcac catcaactgg ccaggcgagt   600
cgggggcatg gtacacgggg ttcattatct acgccttcat cctggggttc ctggtgcccc   660
tcaccatcat ctgtctttgc tacctgttca ttatcatcaa ggtgaagtcc tccggaatcc   720
gagtgggttc ctccaagagg aaaaagtctg agaagaaggt cacccggatg gtgtccattg   780
tggtggccgt cttcattttc tgctggctcc ccttctacat cttcaatgtc tcttcggtct   840
ctgtggccat cagtcccacc ccagccctta aaggcatgtt tgactttgtg gtggtcctca   900
cctatgctaa cagctgtgcc aaccctatcc tctatgcctt cttgtccgac aacttcaaga   960
```

-continued

```
agagcttcca gaatgtcctc tgcttggtca aggtgagcgg cacagatgat ggggaacgga    1020
gtgacagtaa gcaggacaaa tcgcggctga atgagaccac ggagacccag aggaccctcc    1080
tcaatggaga cctccagacc agtatctga                                      1109

<210> SEQ ID NO 5
<211> LENGTH: 20
<212> TYPE: DNA
<213> ORGANISM: Artificial Sequence
<220> FEATURE:
<223> OTHER INFORMATION: Guide sequence

<400> SEQUENCE: 5
tggcgtatga gctactcaac                                                  20

<210> SEQ ID NO 6
<211> LENGTH: 87
<212> TYPE: DNA
<213> ORGANISM: Sus scrofa

<400> SEQUENCE: 6
ttggaactag cctgggactg tcaggcagcc atggatatgg cgtatgagct actcaacggg     60
agccagccgt ggctttcctc tccattc                                          87

<210> SEQ ID NO 7
<211> LENGTH: 84
<212> TYPE: DNA
<213> ORGANISM: Artificial Sequence
<220> FEATURE:
<223> OTHER INFORMATION: Modified Sus scrofa sequence

<400> SEQUENCE: 7
ttggaactag cctgggactg tcaggcagcc atggatatgg cgtatgagct aaacgggagc     60
cagccgtggc tttcctctcc attc                                             84

<210> SEQ ID NO 8
<211> LENGTH: 86
<212> TYPE: DNA
<213> ORGANISM: Artificial Sequence
<220> FEATURE:
<223> OTHER INFORMATION: Modified Sus scrofa sequence

<400> SEQUENCE: 8
ttggaactag cctgggactg tcaggcagcc atggatatgg cgtatgagct actcacggga     60
gccagccgtg gctttcctct ccattc                                           86

<210> SEQ ID NO 9
<211> LENGTH: 84
<212> TYPE: DNA
<213> ORGANISM: Artificial Sequence
<220> FEATURE:
<223> OTHER INFORMATION: Modified Sus scrofa sequence

<400> SEQUENCE: 9
ttggaactag cctgggactg tcaggcagcc atggatatgg cgtatgagct acacgggagc     60
cagccgtggc tttcctctcc attc                                             84

<210> SEQ ID NO 10
<211> LENGTH: 84
<212> TYPE: DNA
<213> ORGANISM: Artificial Sequence
<220> FEATURE:
<223> OTHER INFORMATION: Modified Sus scrofa sequence
```

<400> SEQUENCE: 10
ttggaactag cctgggactg tcaggcagcc atggatatgg cgtatgagct acacgggagc    60
cagccgtggg tttcctctcc attc    84

<210> SEQ ID NO 11
<211> LENGTH: 84
<212> TYPE: DNA
<213> ORGANISM: Artificial Sequence
<220> FEATURE:
<223> OTHER INFORMATION: Modified Sus scrofa sequence

<400> SEQUENCE: 11
ttggaactag cctgggactc tcacgcagcc atggatatgg cgtatgagat aaacgggagc    60
cagccgtggc tttcctctcc attc    84

<210> SEQ ID NO 12
<211> LENGTH: 331
<212> TYPE: PRT
<213> ORGANISM: Sus scrofa

<400> SEQUENCE: 12

Met Asp Met Ala Tyr Glu Leu Leu Asn Gly Ser Gln Pro Trp Leu Ser
1               5                   10                  15

Ser Pro Phe Asp Leu Asn Gly Ser Val Ala Thr Ala Asn Ser Ser Asn
            20                  25                  30

Gln Thr Glu Pro Tyr Tyr Asp Leu Thr Ser Asn Ala Val Leu Thr Phe
        35                  40                  45

Ile Tyr Phe Val Val Cys Ile Ile Gly Leu Cys Gly Asn Thr Leu Val
    50                  55                  60

Ile Tyr Val Ile Leu Arg Tyr Ala Lys Met Lys Thr Ile Thr Asn Ile
65                  70                  75                  80

Tyr Ile Leu Asn Leu Ala Ile Ala Asp Glu Leu Phe Met Leu Gly Leu
                85                  90                  95

Pro Phe Leu Ala Met Gln Val Ala Leu Val His Trp Pro Phe Gly Lys
            100                 105                 110

Ala Ile Cys Arg Val Val Met Thr Val Asp Gly Ile Asn Gln Phe Thr
        115                 120                 125

Ser Ile Phe Cys Leu Thr Val Met Ser Ile Asp Arg Tyr Leu Ala Val
    130                 135                 140

Val His Pro Ile Lys Ser Ala Lys Trp Arg Arg Pro Arg Thr Ala Lys
145                 150                 155                 160

Met Ile Asn Val Ala Val Trp Gly Val Ser Leu Leu Val Ile Leu Pro
                165                 170                 175

Ile Met Ile Tyr Ala Gly Leu Arg Ser Asn Gln Trp Gly Arg Ser Ser
            180                 185                 190

Cys Thr Ile Asn Trp Pro Gly Glu Ser Gly Ala Trp Tyr Thr Gly Phe
        195                 200                 205

Ile Ile Tyr Ala Phe Ile Leu Gly Phe Leu Val Pro Leu Thr Ile Ile
    210                 215                 220

Cys Leu Cys Tyr Leu Phe Ile Ile Lys Val Lys Ser Ser Gly Ile
225                 230                 235                 240

Arg Val Gly Ser Ser Lys Arg Lys Lys Ser Glu Lys Lys Val Thr Arg
                245                 250                 255

Met Val Ser Ile Val Val Ala Val Phe Ile Phe Cys Trp Leu Pro Phe
            260                 265                 270

```
Tyr Ile Phe Asn Val Ser Ser Val Ala Ile Ser Pro Thr Pro
            275                 280                 285

Ala Leu Lys Gly Met Phe Asp Phe Val Val Leu Thr Tyr Ala Asn
    290                 295                 300

Ser Cys Ala Asn Pro Ile Leu Tyr Ala Phe Leu Ser Asp Asn Phe Lys
305                 310                 315                 320

Lys Ser Phe Gln Asn Val Leu Cys Leu Val Lys
                325                 330

<210> SEQ ID NO 13
<211> LENGTH: 39
<212> TYPE: PRT
<213> ORGANISM: Artificial Sequence
<220> FEATURE:
<223> OTHER INFORMATION: Protein sequence of SSTR2 resulting from a 1
      base pair deletion in exon 2

<400> SEQUENCE: 13

Met Asp Met Ala Tyr Glu Leu Leu Thr Gly Ala Ser Arg Gly Phe Pro
1               5                   10                  15

Leu His Ser Thr Ser Met Ala Pro Trp Gln Gln Pro Thr Val Gln Thr
                20                  25                  30

Arg Arg Ser His Thr Met Thr
            35

<210> SEQ ID NO 14
<211> LENGTH: 330
<212> TYPE: PRT
<213> ORGANISM: Artificial Sequence
<220> FEATURE:
<223> OTHER INFORMATION: Protein sequence of SSTR2 resulting from a 3
      base pair in frame deletion in exon 2

<400> SEQUENCE: 14

Met Asp Met Ala Tyr Glu Leu Asn Gly Ser Gln Pro Trp Leu Ser Ser
1               5                   10                  15

Pro Phe Asp Leu Asn Gly Ser Val Ala Thr Ala Asn Ser Ser Asn Gln
                20                  25                  30

Thr Glu Pro Tyr Tyr Asp Leu Thr Ser Asn Ala Val Leu Thr Phe Ile
            35                  40                  45

Tyr Phe Val Val Cys Ile Ile Gly Leu Cys Gly Asn Thr Leu Val Ile
        50                  55                  60

Tyr Val Ile Leu Arg Tyr Ala Lys Met Lys Thr Ile Thr Asn Ile Tyr
65                  70                  75                  80

Ile Leu Asn Leu Ala Ile Ala Asp Glu Leu Phe Met Leu Gly Leu Pro
                85                  90                  95

Phe Leu Ala Met Gln Val Ala Leu His Trp Pro Phe Gly Lys Ala
            100                 105                 110

Ile Cys Arg Val Val Met Thr Val Asp Gly Ile Asn Gln Phe Thr Ser
        115                 120                 125

Ile Phe Cys Leu Thr Val Met Ser Ile Asp Arg Tyr Leu Ala Val Val
    130                 135                 140

His Pro Ile Lys Ser Ala Lys Trp Arg Arg Pro Arg Thr Ala Lys Met
145                 150                 155                 160

Ile Asn Val Ala Val Trp Gly Val Ser Leu Leu Val Ile Leu Pro Ile
                165                 170                 175

Met Ile Tyr Ala Gly Leu Arg Ser Asn Gln Trp Gly Arg Ser Ser Cys
            180                 185                 190
```

-continued

```
Thr Ile Asn Trp Pro Gly Glu Ser Gly Ala Trp Tyr Thr Gly Phe Ile
        195                 200                 205

Ile Tyr Ala Phe Ile Leu Gly Phe Leu Val Pro Leu Thr Ile Ile Cys
        210                 215                 220

Leu Cys Tyr Leu Phe Ile Ile Ile Lys Val Lys Ser Ser Gly Ile Arg
225                 230                 235                 240

Val Gly Ser Ser Lys Arg Lys Lys Ser Glu Lys Lys Val Thr Arg Met
                245                 250                 255

Val Ser Ile Val Val Ala Val Phe Ile Phe Cys Trp Leu Pro Phe Tyr
                260                 265                 270

Ile Phe Asn Val Ser Ser Val Ser Val Ala Ile Ser Pro Thr Pro Ala
        275                 280                 285

Leu Lys Gly Met Phe Asp Phe Val Val Val Leu Thr Tyr Ala Asn Ser
        290                 295                 300

Cys Ala Asn Pro Ile Leu Tyr Ala Phe Leu Ser Asp Asn Phe Lys Lys
305                 310                 315                 320

Ser Phe Gln Asn Val Leu Cys Leu Val Lys
                325                 330
```

LIVESTOCK ANIMALS WITH IMPROVED GROWTH PERFORMANCE

CROSS REFERENCE TO RELATED APPLICATIONS

This application claims priority to provisional application U.S. Ser. No. 62/957,861, filed Jan. 7, 2020, which is incorporated herein by reference in its entirety.

SEQUENCE LISTING

The instant application contains a Sequence Listing which has been submitted in ASCII format via EFS-Web and is hereby incorporated by reference in its entirety. Said ASCII copy, created on Jan. 4, 2021, is named 2021-01-04_ROSS_P13042US01_SEQLISTING_ST25.txt and is 16,515 bytes in size.

TECHNICAL FIELD

The present invention relates to genetically edited livestock animals and the modification of somatostatin receptor genes to provide improved growth performance.

BACKGROUND

Somatostatin (SST) plays a key role in the inhibition of growth hormone (GH), by inhibiting growth hormone releasing hormone (GHRH) in the brain via negative feedback mechanisms. Although many attempts have been made in the past to skew the balance of SST and GHRH in favor of GHRH both by inhibiting SST and overexpressing GH, the ideas were eventually scrapped for various reasons. Even a tiny increase in GH in commercial swine production would result in millions of dollars and thousands of pounds of inputs saved, and a significant reduction in the industry's carbon footprint.

For the swine industry both in the US and abroad, raising pigs that put on more weight in less time has a huge impact on both monetary and feed inputs, as well as lowering the overall carbon footprint of the industry. On the world stage, we are rapidly approaching a time where we will have to produce more animal protein in less time with fewer inputs. Furthermore, demand for pork as a meat source is growing rapidly around the world.

As can be seen, there is a need in the art for pigs and other livestock animals with improved growth performance.

SUMMARY

The present invention provides livestock animals and methods for improving growth performance by creating animals that have modified somatostatin receptor (SSTR) expression or activity. The animals have inactivated or otherwise modified SSTR expression or activity and improved growth performance. The livestock animals can be created using any of a number of protocols such as knockout technology or gene-editing. Thus, an embodiment of the invention is a genetically edited or modified livestock animal or animal cell comprising a genome with inactivation of a SSTR gene. In some embodiments, the modified somatostatin receptor is SSTR2.

Yet another embodiment of the invention is a process of making a livestock animal comprising a livestock animal cell or livestock embryo, an agent that specifically binds to a DNA target site of the cell and causes a double-stranded DNA break or otherwise inactivates a SSTR gene therein using gene editing methods such as the Clustered Regularly Interspaced Short Palindromic Repeats (CRISPR)/Cas system, Transcription Activator-Like Effector Nucleases (TALENs), Zinc Finger Nucleases (ZFN), or recombinase fusion proteins.

Further embodiments will become evident from the detailed description of the invention which follows.

BRIEF DESCRIPTION OF THE FIGURES

FIG. 1 shows the sequence alignment for 74-1. Sequence alignment from top to bottom: Wild type SSTR2, guide RNA target site, 10 sequences obtained after sequencing a TA cloning vector containing the PCR product of the region of interest from 74-1 DNA. Both deletions can be seen at the cut site between the 17th and 18th base pairs of the target site.

FIG. 2 shows the sequence alignment for 74-2. Sequence alignment from top to bottom: Wild type SSTR2, guide RNA target site, 10 sequences obtained after sequencing a TA cloning vector containing the PCR product of the region of interest from 74-1 DNA. Both deletions can be seen at the cut site between the 17th and 18th base pairs of the target site.

FIG. 3A, FIG. 3B, and FIG. 3C show SSTR2 protein sequences. FIG. 3A shows the wild type protein sequence of SSTR2 (SEQ ID NO: 12). FIG. 3B shows the predicted protein sequence of SSTR2 resulting from a 1 base pair deletion in exon 2 (SEQ ID NO: 13). The sequence is altered eight amino acids after the start codon and results in a premature stop codon. FIG. 3C shows the predicted protein sequence of SSTR2 resulting from a 3 base pair, in frame deletion in exon 2 (SEQ ID NO: 14). The sequence lacks a single leucine eight amino acids after the start codon.

DETAILED DESCRIPTION

Figure 4:
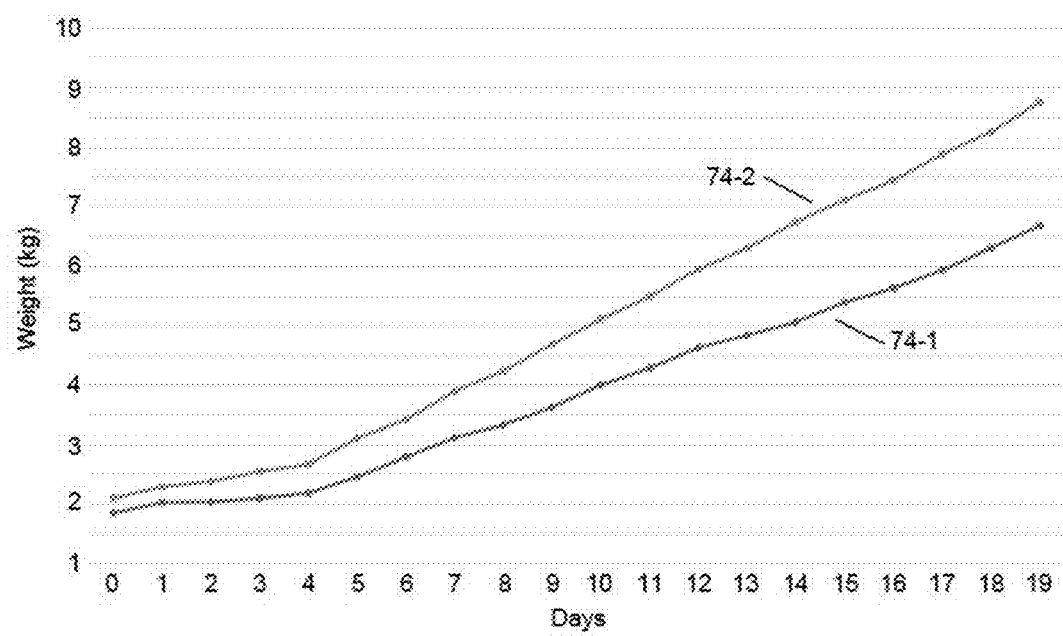
FIG. 4 shows daily body weight. Daily body weights recorded in the morning for 74-1 and 74-2 from birth to day 19. By comparison, approximately 5.5 kg is the average body weight of a piglet at ~18-20 days of age.
Figure 5:
FIG. 5 shows piglets 74-1 (right) and 74-2 (left) at 21 days of age.

The present invention now will be described more fully with reference to the accompanying examples. The invention may be embodied in many different forms and should not be construed as limited to the embodiments set forth in this application; rather, these embodiments are provided so that this disclosure will satisfy applicable legal requirements.

Many modifications and other embodiments of the invention will come to mind to one skilled in the art to which this invention pertains, having the benefit of the teachings presented in the descriptions and the drawings herein. As a result, it is to be understood that the invention is not to be limited to the specific embodiments disclosed and that modifications and other embodiments are intended to be included within the scope of the appended claims. Although specific terms are used in the specification, they are used in a generic and descriptive sense only and not for purposes of limitation.

Units, prefixes, and symbols may be denoted in their SI accepted form. Unless otherwise indicated, nucleic acids are written from left to right in 5' to 3' orientation; amino acid sequences are written from left to right in amino to carboxy orientation, respectively. Numeric ranges recited within the specification are inclusive of the numbers defining the range and include each integer within the defined range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. The terms defined below are more fully defined by reference to the specification as a whole.

The singular terms "a", "an", and "the" include plural referents unless context clearly indicates otherwise. Similarly, the word "or" is intended to include "and" unless the context clearly indicate otherwise. The word "or" means any one member of a particular list and also includes any combination of members of that list.

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e. g., Diagnostic Molecular Microbiology: Principles and Applications, D. H. Persing et al., Ed., American Society for Microbiology, Washington, D.C. (1993). The product of amplification is termed an amplicon.

The term "Cas" refers to a "CRISPR associated" protein. Non-limiting examples of Cas proteins include Cas1, Cas1B, Cas2, Cas3, Cas4, Cas5, Cash, Cas7, Cas8, Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologs thereof, or modified versions thereof.

"Cas9" (formerly referred to as Cas5, Csn1, or Csx12) herein refers to a Cas endonuclease of a type II CRISPR system that forms a complex with a crNucleotide and a tracrNucleotide, or with a single guide polynucleotide, for specifically recognizing and cleaving all or part of a DNA target sequence.

The term "conservatively modified variants" applies to both amino acid and nucleic acid sequences. With respect to particular nucleic acid sequences, "conservatively modified variants" refers to those nucleic acids which encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also, by reference to the genetic code, describes every possible silent variation of the nucleic acid.

One of ordinary skill will recognize that each codon in a nucleic acid (except AUG, which is ordinarily the only codon for methionine; and UGG, which is ordinarily the only codon for tryptophan) can be modified to yield a functionally identical molecule. Accordingly, each silent variation of a nucleic acid which encodes a polypeptide of the present invention is implicit in each described polypeptide sequence and is within the scope of the present invention.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Thus, any number of amino acid residues selected from the group of integers from 1 to 15 can be so altered. Thus, for example, 1, 2, 3, 4, 5, 7, or 10 alterations can be made.

Conservatively modified variants typically provide similar biological activity as the unmodified polypeptide sequence from which they are derived. For example, substrate specificity, enzyme activity, or ligand/receptor binding is generally at least 30%, 40%, 50%, 60%, 70%, 80%, or 90% of the native protein for its native substrate. Conservative substitution tables providing functionally similar amino acids are well known in the art. The following six groups each contain amino acids that are conservative substitutions for one another: [1] Alanine (A), Serine (S), Threonine (T); [2] Aspartic acid (D), Glutamic acid (E); [3] Asparagine (N), Glutamine (Q); [4] Arginine (R), Lysine (K); [5] Isoleucine (I), Leucine (L), Methionine (M), Valine (V); and [6] Phenylalanine (F), Tyrosine (Y), Tryptophan (W). See also, Creighton (1984) Proteins W. H. Freeman and Company.

A "CRISPR system" refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or other sequences and transcripts from a CRISPR locus.

By "encoding" or "encoded", with respect to a specified nucleic acid, is meant comprising the information for translation into the specified protein. A nucleic acid encoding a protein may comprise intervening sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. When the nucleic acid is prepared or altered synthetically, advantage can be taken of known codon preferences of the intended host where the nucleic acid is to be expressed.

As used herein "full-length sequence" in reference to a specified polynucleotide or its encoded protein means having the entire amino acid sequence of a native (nonsynthetic), endogenous, biologically active form of the specified protein. Methods to determine whether a sequence is full-length are well known in the art including such exemplary techniques as northern or western blots, primer extension, S1 protection, and ribonuclease protection. Comparison to known full-length homologous (orthologous and/or paralogous) sequences can also be used to identify full-length sequences of the present invention. Additionally, consensus sequences typically present at the 5' and 3' untranslated regions of mRNA aid in the identification of a polynucleotide as full-length. For example, the consensus sequence ANNNNAUGG, where the underlined codon represents the N-terminal methionine, aids in determining whether the polynucleotide has a complete 5' end. Consensus sequences at the 3' end, such as polyadenylation sequences, aid in determining whether the polynucleotide has a complete 3' end.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by deliberate human intervention.

By "host cell" is meant a cell which contains a vector and supports the replication and/or expression of the vector. Host cells may be prokaryotic cells such as E. coli, or eukaryotic cells such as yeast, insect, amphibian, or mammalian cells.

The term "hybridization complex" includes reference to a duplex nucleic acid structure formed by two single-stranded nucleic acid sequences selectively hybridized with each other.

The term "introduced" in the context of inserting a nucleic acid into a cell is equivalent to "transfection" or "transformation" or "transduction," and includes reference to the incorporation of a nucleic acid into a eukaryotic or prokaryotic cell where the nucleic acid may be incorporated into the genome of the cell (e. g., chromosome, plasmid, plastid or mitochondrial DNA), converted into an autonomous replicon, or transiently expressed (e.g., transfected mRNA).

The term "isolated" refers to material, such as a nucleic acid or a protein, which is: (1) substantially or essentially free from components that normally accompany or interact with it as found in its naturally occurring environment—the isolated material optionally comprises material not found with the material in its natural environment; or (2) if the material is in its natural environment, the material has been synthetically altered by deliberate human intervention to a composition and/or placed at a location in the cell (e.g., genome or subcellular organelle) not native that material. The alteration to yield the synthetic material can be performed on the material within, or removed from its natural state. For example, a naturally occurring nucleic acid becomes an isolated nucleic acid if it is altered, or if it is transcribed from DNA which has been altered, by means of human intervention performed within the cell from which it originates. See, e.g., Compounds and Methods for Site Directed Mutagenesis in Eukaryotic Cells, Kmiec, U.S. Pat. No. 5,565,350; In Vivo Homologous Sequence Targeting in Eukaryotic Cells; Zarling et al., PCT/US93/03868. Likewise, a naturally occurring nucleic acid (e.g., a promoter) becomes isolated if it is introduced by non-naturally occurring means to a locus of the genome not native to that nucleic acid. Nucleic acids which are "isolated" as defined herein, are also referred to as "heterologous" nucleic acids.

As used herein, "marker" includes reference to a locus on a chromosome that serves to identify a unique position on the chromosome. A "polymorphic marker" includes reference to a marker which appears in multiple forms (alleles) such that different forms of the marker, when they are present in a homologous pair, allow transmission of each of the chromosomes of that pair to be followed. A genotype may be defined by use of one or a plurality of markers.

As used herein, "mutation" includes reference to alterations in the nucleotide sequence of a polynucleotide, for example a gene or coding DNA sequence (CDS), compared to the wild-type sequence. The term includes, without limitation, substitutions, insertions, frameshifts, deletions, inversions, translocations, duplications, splice-donor site mutations, point-mutations or the like.

As used herein, "nucleic acid" includes reference to a deoxyribonucleotide or ribonucleotide polymer in either single- or double-stranded form, and unless otherwise limited, encompasses conservatively modified variants and known analogues having the essential nature of natural nucleotides in that they hybridize to single-stranded nucleic acids in a manner similar to naturally occurring nucleotides (e. g., peptide nucleic acids).

By "nucleic acid library" is meant a collection of isolated DNA or RNA molecules which comprise and substantially represent the entire transcribed fraction of a genome of a specified organism. Construction of exemplary nucleic acid libraries, such as genomic and cDNA libraries, is taught in standard molecular biology references such as Berger and Kimmel, Guide to Molecular Cloning Techniques, Methods in Enzymology, Vol. 152, Academic Press, Inc., San Diego, Calif. (Berger); Sambrook et al., Molecular Cloning-A Laboratory Manual, 2nded., Vol. 1-3 (1989); and Current Protocols in Molecular Biology, F. M. Ausubel et al., Eds., Current Protocols, a joint venture between Greene Publishing Associates, Inc. and John Wiley & Sons, Inc. (1994).

As used herein "operably linked" includes reference to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary join two protein coding regions, contiguously and in the same reading frame.

As used herein, "polynucleotide" includes reference to a deoxyribopolynucleotide, ribopolynucleotide, or conservatively modified variants; the term may also refer to analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art.

The term polynucleotide as it is employed herein embraces such chemically, enzymatically or metabolically modified forms of polynucleotides, as well as the chemical forms of DNA and RNA characteristic of viruses and cells, including among other things, simple and complex cells.

The terms "polypeptide", "peptide" and "protein" are used interchangeably herein to refer to a polymer of amino acid residues. The terms also may apply to conservatively modified variants and to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, the protein is specifically reactive to antibodies elicited to the same protein but consisting entirely of naturally occurring amino acids. The terms "polypeptide", "peptide" and "protein" are also inclusive of modifications including, but not limited to, glycosylation, lipid attachment, sulfation, gamma-carboxylation of glutamic acid residues, hydroxylation and ADP-ribosylation. It will be appreciated, as is well known and as noted above, that polypeptides are not always entirely linear. For instance, polypeptides may be branched as a result of ubiquitization, and they may be circular, with or without branching, generally as a result of posttranslation events, including natural processing event and events brought about by human manipulation which do not occur naturally. Circular, branched and branched circular polypeptides may be synthesized by non-translation natural process and by entirely synthetic methods, as well. Further, this invention contemplates the use of both the methionine-containing and the methionine-less amino terminal variants of the protein of the invention.

As used herein "promoter" includes reference to a region of DNA upstream from the start of transcription and involved in recognition and binding of RNA polymerase and other proteins to initiate transcription. Examples of promoters under developmental control include promoters that preferentially initiate transcription in certain tissues, such as testes, ovaries, or placenta. Such promoters are referred to as "tissue preferred". Promoters which initiate transcription only in certain tissue are referred to as "tissue specific". A "cell type" specific promoter primarily drives expression in certain cell types in one or more organs, for example, germ cells in testes or ovaries. An "inducible" or "repressible" promoter is a promoter which is under environmental control. Examples of environmental conditions that may affect transcription by inducible promoters include stress, and temperature. Tissue specific, tissue preferred, cell type specific and inducible promoters constitute the class of "non-constitutive" promoters. A "constitutive" promoter is a promoter which is active under most environmental conditions.

As used herein "recombinant" includes reference to a cell or vector, that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, under-expressed or not expressed at all as a result of deliberate human intervention. The term "recombinant" as used herein does not encompass the alteration of the cell or vector by naturally occurring events (e.g., spontaneous mutation, natural transformation/transduction/transposition) such as those occurring without deliberate human intervention.

As used herein, a "recombinant expression cassette" is a nucleic acid construct, generated recombinantly or synthetically, with a series of specified nucleic acid elements which permit transcription of a particular nucleic acid in a host cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid to be transcribed, and a promoter.

The terms "residue" or "amino acid residue" or "amino acid" are used interchangeably herein to refer to an amino acid that is incorporated into a protein, polypeptide, or peptide (collectively "protein"). The amino acid may be a naturally occurring amino acid and, unless otherwise limited, may encompass non-natural analogs of natural amino acids that can function in a similar manner as naturally occurring amino acids.

The term "selectively hybridizes" includes reference to hybridization, under stringent hybridization conditions, of a nucleic acid sequence to another nucleic acid sequence or other biologics. When utilizing a hybridization-based detection system, a nucleic acid probe is chosen that is complementary to a reference nucleic acid sequence, and then by selection of appropriate conditions the probe and the reference sequence selectively hybridize, or bind, to each other to form a duplex molecule.

The term "stringent conditions" or "stringent hybridization conditions" includes reference to conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences can be identified which are 100% complementary to the probe (homologous probing).

Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e. g., 10 to 50 nucleotides) and at least about 60° C. for long probes (e.g., greater than 50 nucleotides). Stringent conditions may also be achieved with the addition of destabilizing agents such as formamide. Specificity is typically the function of post-hybridization washes, the critical factors being the ionic strength and temperature of the final wash solution. For DNA/DNA hybrids, the thermal melting point (Tm) can be approximated from the equation of Meinkoth and Wahl, Anal. Biochem., 138: 267-284 (1984): Tm [° C.]=81.5+16.6 (log M)+0.41 (% GC)-0.61 (% form)-500/L; where M is the molarity of monovalent cations, % GC is the percentage of guanosine and cytosine nucleotides in the DNA, % form is the percentage of formamide in the hybridization solution, and L is the length of the hybrid in base pairs. The Tm is the temperature (under defined ionic strength and pH) at which 50% of a complementary target sequence hybridizes to a perfectly matched probe. Tm is reduced by about 1° C. for each 1% of mismatching; thus, Tm, hybridization and/or wash conditions can be adjusted to hybridize to sequences of the desired identity. For example, if sequences with >90% identity are sought, the Tm can be decreased 10° C. Generally, stringent conditions are selected to be about 5° C. lower than the Tm for the specific sequence and its complement at a defined ionic strength and pH. However, severely stringent conditions can utilize a hybridization and/or wash at 1 to 4° C. lower than the Tm; moderately stringent conditions can utilize a hybridization and/or wash at 6 to 10° C. lower than the Tm; low stringency conditions can utilize a hybridization and/or wash at 11 to 20° C. lower than the Tm. Using the equation, hybridization and wash compositions, and desired Tm, those of ordinary skill will understand that variations in the stringency of hybridization and/or wash solutions are inherently described. An extensive guide to the hybridization of nucleic acids is found in Tijssen, Laboratory Techniques in Biochemistry and Molecular Biology—Hybridization with Nucleic Acid Probes, Part I, Chapter 2 "Overview of principles of hybridization and the strategy of nucleic acid probe assays", Elsevier, New York (1993); and Current Protocols in Molecular Biology, Chapter 2, Ausubel, et al., Eds., Greene Publishing and Wiley-Interscience, New York (1995).

As used herein, "transgenic animal, cell or tissue" includes reference to an animal which includes within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette.

"Transgenic" is used herein to include any cell, cell line, tissue, or organ, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extrachromosomal) by conventional breeding methods or by naturally occurring events such as random cross-fertilization, non-recombinant viral infection, non-recombinant bacterial transformation, non-recombinant transposition, or spontaneous mutation.

As used herein, "vector" includes reference to a nucleic acid used in transfection of a host cell and into which can be inserted a polynucleotide. Vectors are often replicons. Expression vectors permit transcription of a nucleic acid inserted therein.

The following terms are used to describe the sequence relationships between a polynucleotide/polypeptide of the present invention with a reference polynucleotide/polypeptide: (a)"reference sequence", (b)"comparison window", (c) "sequence identity", and (d)"percentage of sequence identity".

(a) As used herein, "reference sequence" is a defined sequence used as a basis for sequence comparison with a polynucleotide/polypeptide of the present invention. A reference sequence may be a subset or the entirety of a specified sequence; for example, as a segment of a full-length cDNA or gene sequence, or the complete cDNA or gene sequence.

(b) As used herein, "comparison window" includes reference to a contiguous and specified segment of a polynucleotide/polypeptide sequence, wherein the polynucleotide/polypeptide sequence may be compared to a reference sequence and wherein the portion of the polynucleotide/polypeptide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides/amino acids residues in length, and optionally can be 30, 40, 50, 100, or longer. Those of skill in the art understand that to avoid a high similarity to a reference sequence due to inclusion of gaps in the polynucleotide/polypeptide sequence, a gap penalty is typically introduced and is subtracted from the number of matches.

Methods of alignment of sequences for comparison are well-known in the art. Optimal alignment of sequences for comparison may be conducted by the local homology algorithm of Smith and Waterman, Adv. Appl. Math. 2: 482 (1981); by the homology alignment algorithm of Needleman and Wunsch, J. Mol. Biol. 48: 443 (1970); by the search for similarity method of Pearson and Lipman, Proc. Natl. Acad. Sci. 85: 2444 (1988); and by computerized implementations of these algorithms, including, but not limited to: CLUSTAL in the PC/Gene program by Intelligenetics, Mountain View, Calif.; GAP, BESTFIT, BLAST, FASTA, and TFASTA, and related programs in the GCG Wisconsin Genetics Software Package, Version 10 (available from Accelrys Inc., 9685 Scranton Road, San Diego, Calif., USA). The CLUSTAL program is well described by Higgins and Sharp, Gene 73: 237-244 (1988); Higgins and Sharp, CABIOS 5: 151-153 (1989); Corpet, et al., Nucleic Acids Research 16: 10881-90 (1988); Huang, et al., Computer Applications in the Biosciences 8: 155-65 (1992), and Pearson, et al., Methods in Molecular Biology 24: 307-331 (1994).

The BLAST family of programs that can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, Current Protocols in Molecular Biology, Chapter 19, Ausubel, et al., Eds., Greene Publishing and Wiley-Interscience, New York (1995); Altschul et al., J. Mol. Biol., 215: 403-410 (1990); and, Altschul et al., Nucleic Acids Res. 25: 3389-3402 (1997). Software for performing BLAST analyses is publicly available, for example through the National Center for Biotechnology Information (ncbi.nlm.nih.gov/). This algorithm has been thoroughly described in a number of publications. See, e.g., Altschul S F et al., Gapped BLAST and PSI-BLAST: a new generation of protein database search programs, 25 NUCLEIC ACIDS RES. 3389 (1997); National Center for Biotechnology Information, THE NCBI HANDBOOK [INTERNET], Chapter 16: The BLAST Sequence Analysis Tool (McEntyre J, Ostell J, eds., 2002), available on the world wide web at ncbi.nlm.nih.gov/books/NBK21097/pdf/ch16.pdf. The BLASTP program for amino acid sequences has also been thoroughly described (see Henikoff & Henikoff (1989) Proc. Natl. Acad. Sci. USA 89: 10915).

In addition to calculating percent sequence identity, the BLAST algorithm also performs a statistical analysis of the similarity between two sequences (see, e.g., Karlin & Altschul, Proc. Nat'l. Acad. Sci. USA 90: 5873-5877 (1993)). A number of low-complexity filter programs can be employed to reduce such low-complexity alignments. For example, the SEG (Wooten and Federhen, Comput. Chem., 17: 149-163 (1993)) and XNU (Claverie and States, Comput. Chem., 17: 191-201 (1993)) low-complexity filters can be employed alone or in combination.

Multiple alignment of the sequences can be performed using the CLUSTAL method of alignment (Higgins and Sharp (1989) CABIOS. 5: 151-153) with the default parameters (GAP PENALTY=10, GAP LENGTH PENALTY=10).

Default parameters for pairwise alignments using the CLUSTAL method include KTUPLE 1, GAP PENALTY=3, WINDOW=5 and DIAGONALS SAVED=5.

(c) As used herein, "sequence identity" or "identity" in the context of two nucleic acid or polypeptide sequences includes reference to the residues in the two sequences which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions may be calculated according to the algorithm of Meyers and Miller, Computer Applic. Biol. Sci., 4: 11-17 (1988), for example as implemented in the program PC/GENE (Intelligenetics, Mountain View, Calif., USA).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

As used herein, "gene editing," "gene edited" "genetically edited" and "gene editing effectors" refer to the use of naturally occurring or artificially engineered nucleases, also referred to as "molecular scissors." The nucleases create specific double-stranded break (DSBs) at desired locations in the genome, which in some cases harnesses the cell's endogenous mechanisms to repair the induced break by natural processes of homologous recombination (HR) and/or nonhomologous end-joining (NHEJ). Gene editing effectors include Zinc Finger Nucleases (ZFNs), Transcription Activator-Like Effector Nucleases (TALENs), the Clustered Regularly Interspaced Short Palindromic Repeats/Cas (CRISPR/Cas) system, and meganuclease re-engineered as homing endonucleases.

The terms "genetic manipulation" and "genetically manipulated" include gene editing techniques, as well as and/or in addition to other techniques and processes that alter or modify the nucleotide sequence of a gene or gene, or modify or alter the expression of a gene or genes.

As used herein "homing DNA technology" or "homing technology" covers any mechanisms that allow a specified molecule to be targeted to a specified DNA sequence including Zinc Finger (ZF) proteins, Transcription Activator-Like Effectors (TALEs), meganucleases, and CRISPR systems (e.g., CRISPR/Cas9 systems).

The term "livestock animal" includes animals traditionally raised in livestock farming, such as beef cattle, dairy cattle, pigs, sheep, goats, horses, mules, asses, buffalo, and camels. The term also includes birds raised commercially for meat or eggs (i.e., chickens, turkeys, ducks, geese, guinea fowl, and squabs). This does not include rats, mice, or other rodents.

As used herein "blastocyst" means an early developmental stage of embryo comprising of inner cell mass (from which embryo proper arises) and a fluid filled cavity typically surrounded by a single layer of trophoblast cells. "Developmental Biology", sixth edition, ed. by Scott F. Gilbert, Sinauer Associates, Inc., Publishers, Sunderland, Mass. (2000)

As used herein "conditional knock-out" or "conditional mutation" means when the knock-out or mutation is achieved when certain conditions are met. These conditions include but are not limited to the presence of certain inducing agents, recombinases, antibiotics, and certain temperature or salt levels.

The term "early stage embryo" means any embryo at embryonic stages between fertilized ovum and blastocyst. Typically, eight cell stage and morula stage embryos are referred to as early stage embryos.

The phrase "genetically edited" means those animals or embryos or cells which have a desired genetic modification such as a knock-out, knock-in, conditional, inducible, transient or point mutation(s) of any gene or its regulatory mechanism or a transgenic with foreign or modified gene/s or regulatory sequences, or having undergone genomic modification in any way including but not limited to recombination, chromosomal deletion, addition, translocation, rearrangement or addition, deletion or modification of nucleic acid, protein or any other natural or synthetic molecule or organelle, or cytoplasmic or nuclear transfer, leading to inheritable changes.

As used herein, the term "knock-in" means replacement of an endogenous gene with a transgene or with same endogenous gene with some structural modification/s, but retaining the transcriptional control of the endogenous gene.

"Knock-out" means disruption of the structure or regulatory mechanism of a gene.

Knock-outs may be generated through homologous recombination of targeting vectors, replacement vectors or hit-and-run vectors or random insertion of a gene trap vector resulting into complete, partial or conditional loss of gene function. "Oogenesis" means the process of generation of mature eggs from the primordial germ cells in females.

"Wild type" means those animals, embryos, or cells derived therefrom, which have not been genetically edited and are usually inbred and outbred strains developed from naturally occurring strains.

The term "growth performance" is known in the art as a reference to the criteria of growth rate of an animal. The "growth rate" or "weight gain" of an animal is the rate of unit gain in live weight of the animal. Growth rate or weight gain is obtained from successive measurements of live weight over a certain period of time. Accordingly, in the present invention the term "growth performance" means an improvement or increase in growth rate or weight gain over time of an animal.

A "binding protein" is a protein that is able to bind to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

A "TALE DNA binding domain" or "TALE" is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein.

Zinc finger and TALE binding domains can be "engineered" to bind to a predetermined nucleotide sequence, for example via engineering (altering one or more amino acids) of the recognition helix region of naturally occurring zinc finger or TALE proteins. Therefore, engineered DNA binding proteins (zinc fingers or TALEs) are proteins that are non-naturally occurring. Non-limiting examples of methods for engineering DNA-binding proteins are design and selection. A designed DNA binding protein is a protein not occurring in nature whose design/composition results principally from rational criteria. Rational criteria for design include application of substitution rules and computerized algorithms for processing information in a database storing information of existing ZFP and/or TALE designs and binding data. See, for example, U.S. Pat. Nos. 6,140,081; 6,453,242; and 6,534,261; see also WO 98/53058; WO 98/53059; WO 98/53060; WO 02/016536 and WO 03/016496 and U.S. Publication No. 20110301073.

A "selected" zinc finger protein or TALE is a protein not found in nature whose production results primarily from an empirical process such as phage display, interaction trap or hybrid selection. See e.g., U.S. Pat. Nos. 5,789,538; 5,925,523; 6,007,988; 6,013,453; 6,200,759; WO 95/19431; WO 96/06166; WO 98/53057; WO 98/54311; WO 00/27878; WO 01/60970 WO 01/88197, WO 02/099084 and U.S. Publication No. 20110301073.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and − cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain). See, also, U.S. Patent Publication Nos. 2005/0064474, 20070218528, 2008/0131962 and 2011/0201055, incorporated herein by reference in their entireties.

Somatostatin Receptor Gene Editing

Somatostatin (SST) is a highly conserved peptide found in tissues throughout the body of many species including fish, livestock, and humans. Through its two forms and five receptors, SST acts as a potent inhibitor of growth hormone (GH), insulin, glucagon, and thyroid stimulating hormone. Produced and released from the hypothalamus in response to GH levels, SST is transported to the anterior pituitary where it blocks the production of GH by somatotrophs and/or the blocks the release of GH from the cells.

Various somatostatin receptor knockout mutants in mice were previously characterized and no increases in growth rate or size were reported. SSTR1 gene-ablated mice exhibited significantly reduced body weight with growth retardation compared to wild type controls (Wang et al. 2006. Mol Cell Endocrinol. 247:82-90). Heterozygous SSTR2 knockouts were indistinguishable from their normal littermates, and the homozygotes appeared normal and healthy up to 15 months of age (Zheng et al. 1997. Mol Endocrinol 11:1709-1717). In contrast to these previous studies in mice, Applicants have unexpectedly demonstrated that a SSTR2 knockout provides opportunity for improved growth performance in pigs that has not been observed in other species.

The SST receptor family of genes is known and sequences encoding the same are available through Genbank or other such sources. *Sus scrofa* SSTR2 nucleic acid and protein sequences are disclosed as SEQ ID NOs: 1 and 2.

The present disclosure provides a genetically edited animal or animal cell comprising at least one edited chromosomal sequence encoding a somatostatin receptor protein. The edited chromosomal sequence may be (1) inactivated, (2) modified, or (3) comprise an integrated or deleted sequence. An inactivated chromosomal sequence is altered such that a somatostatin receptor protein function is impaired, reduced or eliminated. Thus, a genetically edited animal comprising an inactivated chromosomal sequence may be termed a "knock out" or a "conditional knock out." Similarly, a genetically edited animal comprising an integrated sequence may be termed a "knock in" or a "conditional knock in." Furthermore, a genetically edited animal comprising a modified chromosomal sequence may comprise a targeted point mutation(s) or other modification such that an altered protein product is produced.

In some embodiments of the present invention, at least one somatostatin receptor locus (e.g., a SSTR2 locus) is used as a target site for the site-specific editing. This can include insertion of an exogenous nucleic acid (e.g., a nucleic acid comprising a nucleotide sequence encoding a polypeptide of interest) or deletions of nucleic acids from the locus. In particular embodiments, insertions and/or deletions modified locus. For example, integration of the exogenous nucleic acid and/or deletion of part of the genomic nucleic acid may modify the locus so as to produce a disrupted (i.e., inactivated) SSTR gene.

In some embodiments, the edited SSTR locus can comprise the nucleotide sequence set forth in SEQ ID NOs: 3 or 4. In some embodiments, the edited SSTR locus may comprise a nucleotide sequence that is substantially identical to the nucleotide sequence set forth in SEQ ID NOs: 3 or 4. For example, in some embodiments, a SSTR locus is a SSTR homologue (e.g., an ortholog or a paralog) that comprises a nucleotide sequence that is at least 85% identical to the nucleotide sequence set forth in SEQ ID NOs: 3 or 4. A SSTR homologue may comprise a nucleotide sequence that is, for example and without limitation: at least 80%; at least 85%; at least about 90%; at least about 91%; at least about 92%; at least about 93%; at least about 94%; at least about 95%; at least about 96%; at least about 97%; at least about 98%; at least about 99%; at least about 99.5%; 99.6%, 99.7%, 99.8% and/or at least about 99.9% identical to about 20 contiguous nucleotides of the nucleotide sequence set forth in SEQ ID NOs: 3 or 4. In some embodiments, the edited chromosomal sequence comprises one or more of SEQ ID NOs: 7-11.

Targeted Integration of a Nucleic Acid at a SSTR Locus

Site-specific integration of an exogenous nucleic acid at a SSTR locus may be accomplished by any technique known to those of skill in the art. In some embodiments, integration of an exogenous nucleic acid at a SSTR locus comprises contacting a cell (e.g., an isolated cell or a cell in a tissue or organism) with a nucleic acid molecule comprising the exogenous nucleic acid. In examples, such a nucleic acid molecule may comprise nucleotide sequences flanking the exogenous nucleic acid that facilitate homologous recombination between the nucleic acid molecule and at least one SSTR locus. In particular examples, the nucleotide sequences flanking the exogenous nucleic acid that facilitate homologous recombination may be complementary to endogenous nucleotides of the SSTR locus. In particular examples, the nucleotide sequences flanking the exogenous nucleic acid that facilitate homologous recombination may be complementary to previously integrated exogenous nucleotides. In some embodiments, a plurality of exogenous nucleic acids may be integrated at one SSTR locus, such as in gene stacking.

Integration of a nucleic acid at a SSTR locus may be facilitated (e.g., catalyzed) in some embodiments by endogenous cellular machinery of a host cell, such as, for example and without limitation, endogenous DNA and endogenous recombinase enzymes. In some embodiments, integration of a nucleic acid at a SSTR locus may be facilitated by one or more factors (e.g., polypeptides) that are provided to a host cell. For example, nuclease(s), recombinase(s), and/or ligase polypeptides may be provided (either independently or as part of a chimeric polypeptide) by contacting the polypeptides with the host cell, or by expressing the polypeptides within the host cell. Accordingly, in some examples, a nucleic acid comprising a nucleotide sequence encoding at least one nuclease, recombinase, and/or ligase polypeptide may be introduced into the host cell, either concurrently or sequentially with a nucleic acid to be integrated site-specifically at a SSTR locus, wherein the at least one nuclease, recombinase, and/or ligase polypeptide is expressed from the nucleotide sequence in the host cell.

DNA-Binding Polypeptides

In some embodiments, site-specific integration may be accomplished by utilizing factors that are capable of recognizing and binding to particular nucleotide sequences, for example, in the genome of a host organism. For instance, many proteins comprise polypeptide domains that are capable of recognizing and binding to DNA in a site-specific manner. A DNA sequence that is recognized by a DNA-binding polypeptide may be referred to as a "target" sequence. Polypeptide domains that are capable of recognizing and binding to DNA in a site-specific manner generally fold correctly and function independently to bind DNA in a site-specific manner, even when expressed in a polypeptide other than the protein from which the domain was originally isolated. Similarly, target sequences for recognition and binding by DNA-binding polypeptides are generally able to be recognized and bound by such polypeptides, even when present in large DNA structures (e.g., a chromosome), particularly when the site where the target sequence is located is one known to be accessible to soluble cellular proteins (e.g., a gene).

While DNA-binding polypeptides identified from proteins that exist in nature typically bind to a discrete nucleotide sequence or motif (e.g., a consensus recognition sequence), methods exist and are known in the art for modifying many such DNA-binding polypeptides to recognize a different nucleotide sequence or motif DNA-binding polypeptides include, for example and without limitation: zinc finger DNA-binding domains; leucine zippers; UPA DNA-binding domains; GAL4; TAL; LexA; a Tet repressor; LacR; and a steroid hormone receptor.

In some examples, a DNA-binding polypeptide is a zinc finger. Individual zinc finger motifs can be designed to target and bind specifically to any of a large range of DNA sites. Canonical $Cys_2His_2$ (as well as non-canonical $Cys_3His$) zinc finger polypeptides bind DNA by inserting an α-helix into the major groove of the target DNA double helix. Recognition of DNA by a zinc finger is modular; each finger contacts primarily three consecutive base pairs in the target, and a few key residues in the polypeptide mediate recognition. By including multiple zinc finger DNA-binding domains in a targeting endonuclease, the DNA-binding specificity of the targeting endonuclease may be further increased (and hence the specificity of any gene regulatory effects conferred thereby may also be increased). See, e.g., Urnov et al. (2005) Nature 435:646-51. Thus, one or more zinc finger DNA-binding polypeptides may be engineered and utilized such that a targeting endonuclease introduced into a host cell interacts with a DNA sequence that is unique within the genome of the host cell.

Preferably, the zinc finger protein is non-naturally occurring in that it is engineered to bind to a target site of choice. See, for example, See, for example, Beerli et al. (2002) Nature Biotechnol. 20:135-141; Pabo et al. (2001) Ann. Rev. Biochem. 70:313-340; Isalan et al. (2001) Nature Biotechnol. 19:656-660; Segal et al. (2001) Curr. Opin. Biotechnol. 12:632-637; Choo et al. (2000) Curr. Opin. Struct. Biol. 10:411-416; U.S. Pat. Nos. 6,453,242; 6,534,261; 6,599,692; 6,503,717; 6,689,558; 7,030,215; 6,794,136; 7,067,317; 7,262,054; 7,070,934; 7,361,635; 7,253,273; and U.S. Patent Publication Nos. 2005/0064474; 2007/0218528; 2005/0267061, all incorporated herein by reference in their entireties.

An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, U.S. Pat. Nos. 6,453,242 and 6,534,261, incorporated by reference herein in their entireties.

Exemplary selection methods, including phage display and two-hybrid systems, are disclosed in U.S. Pat. Nos. 5,789,538; 5,925,523; 6,007,988; 6,013,453; 6,410,248;

6,140,466; 6,200,759; and 6,242,568; as well as WO 98/37186; WO 98/53057; WO 00/27878; WO 01/88197 and GB 2,338,237. In addition, enhancement of binding specificity for zinc finger binding domains has been described, for example, in WO 02/077227.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

Selection of target sites; ZFPs and methods for design and construction of fusion proteins (and polynucleotides encoding same) are known to those of skill in the art and described in detail in U.S. Pat. Nos. 61,400,815; 789,538; 6,453,242; 6,534,261; 5,925,523; 6,007,988; 6,013,453; 6,200,759; WO 95/19431; WO 96/06166; WO 98/53057; WO 98/54311; WO 00/27878; WO 01/60970 WO 01/88197; WO 02/099084; WO 98/53058; WO 98/53059; WO 98/53060; WO 02/016536 and WO 03/016496.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

In some examples, a DNA-binding polypeptide is a DNA-binding domain from GAL4. GAL4 is a modular transactivator in *Saccharomyces cerevisiae*, but it also operates as a transactivator in many other organisms. See, e.g., Sadowski et al. (1988) Nature 335:563-4. In this regulatory system, the expression of genes encoding enzymes of the galactose metabolic pathway in *S. cerevisiae* is stringently regulated by the available carbon source. Johnston (1987) Microbiol. Rev. 51:458-76. Transcriptional control of these metabolic enzymes is mediated by the interaction between the positive regulatory protein, GAL4, and a 17 bp symmetrical DNA sequence to which GAL4 specifically binds (the UAS).

Native GAL4 consists of 881 amino acid residues, with a molecular weight of 99 kDa. GAL4 comprises functionally autonomous domains, the combined activities of which account for activity of GAL4 in vivo. Ma and Ptashne (1987) Cell 48:847-53); Brent and Ptashne (1985) Cell 43 (3 Pt 2):729-36. The N-terminal 65 amino acids of GAL4 comprise the GAL4 DNA-binding domain. Keegan et al. (1986) Science 231:699-704; Johnston (1987) Nature 328: 353-5. Sequence-specific binding requires the presence of a divalent cation coordinated by 6 Cys residues present in the DNA binding domain. The coordinated cation-containing domain interacts with and recognizes a conserved CCG triplet at each end of the 17 bp UAS via direct contacts with the major groove of the DNA helix. Marmorstein et al. (1992) Nature 356:408-14. The DNA-binding function of the protein positions C-terminal transcriptional activating domains in the vicinity of the promoter, such that the activating domains can direct transcription.

Additional DNA-binding polypeptides that may be utilized in certain embodiments include, for example and without limitation, a binding sequence from a AVRBS3-inducible gene; a consensus binding sequence from a AVRBS3-inducible gene or synthetic binding sequence engineered therefrom (e.g., UPA DNA-binding domain); TAL; LexA (see, e.g., Brent & Ptashne (1985), supra); LacR (see, e.g., Labow et al. (1990) Mol. Cell. Biol. 10:3343-56; Baim et al. (1991) Proc. Natl. Acad. Sci. USA 88(12):5072-6); a steroid hormone receptor (Ellliston et al. (1990) J. Biol. Chem. 265:11517-121); the Tet repressor (U.S. Pat. No. 6,271,341) and a mutated Tet repressor that binds to a tet operator sequence in the presence, but not the absence, of tetracycline (Tc); the DNA-binding domain of NF-κB; and components of the regulatory system described in Wang et al. (1994) Proc. Natl. Acad. Sci. USA 91(17):8180-4, which utilizes a fusion of GAL4, a hormone receptor, and VP16.

In certain embodiments, the DNA-binding domain of one or more of the nucleases used in the methods and compositions described herein comprises a naturally occurring or engineered (non-naturally occurring) TAL effector DNA binding domain. See, e.g., U.S. Patent Publication No. 20110301073, incorporated by reference in its entirety herein. In other embodiments, the nuclease comprises a CRISPR system. The CRISPR (clustered regularly interspaced short palindromic repeats) locus, which encodes RNA components of the system, and the Cas (CRISPR-associated) locus, which encodes proteins (Jansen et al., 2002. Mol. Microbiol. 43: 1565-1575; Makarova et al., 2002. Nucleic Acids Res. 30: 482-496; Makarova et al., 2006. Biol. Direct 1: 7; Haft et al., 2005. PLoS Comput. Biol. 1: e60) make up the gene sequences of the CRISPR/Cas nuclease system. CRISPR loci in microbial hosts contain a combination of Cas genes as well as non-coding RNA elements capable of programming the specificity of the CRISPR-mediated nucleic acid cleavage.

The Type II CRISPR is one of the most well characterized systems and carries out targeted DNA double-strand break in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA:tracrRNA complex directs Cas9 to the target DNA via Wastson-Crick base-pairing between the spacer on the crRNA and the protospacer on the target DNA next to the protospacer adjacent motif (PAM), an additional requirement for target recognition. Finally, Cas9 mediates cleavage of target DNA to create a double-stranded break within the protospacer. Activity of the CRISPR/Cas system comprises of three steps: (i) insertion of alien DNA sequences into the CRISPR array to prevent future attacks, in a process called 'adaptation', (ii) expression of the relevant proteins, as well as expression and processing of the array, followed by (iii) RNA-mediated interference with the foreign nucleic acid. Thus, in the bacterial cell, several Cas proteins are involved with the natural function of the CRISPR/Cas system and serve roles in functions such as insertion of the foreign DNA etc.

In certain embodiments, Cas protein may be a "functional derivative" of a naturally occurring Cas protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative to hydrolyze a DNA substrate into fragments. The term "derivative"

encompasses both amino acid sequence variants of polypeptide, covalent modifications, and fusions thereof. Suitable derivatives of a Cas polypeptide or a fragment thereof include but are not limited to mutants, fusions, covalent modifications of Cas protein or a fragment thereof. Cas protein, which includes Cas protein or a fragment thereof, as well as derivatives of Cas protein or a fragment thereof, may be obtainable from a cell or synthesized chemically or by a combination of these two procedures. The cell may be a cell that naturally produces Cas protein, or a cell that naturally produces Cas protein and is genetically engineered to produce the endogenous Cas protein at a higher expression level or to produce a Cas protein from an exogenously introduced nucleic acid, which nucleic acid encodes a Cas that is same or different from the endogenous Cas. In some case, the cell does not naturally produce Cas protein and is genetically engineered to produce a Cas protein.

In particular embodiments, a DNA-binding polypeptide specifically recognizes and binds to a target nucleotide sequence comprised within a genomic nucleic acid of a host organism. Any number of discrete instances of the target nucleotide sequence may be found in the host genome in some examples. The target nucleotide sequence may be rare within the genome of the organism (e.g., fewer than about 10, about 9, about 8, about 7, about 6, about 5, about 4, about 3, about 2, or about 1 copy(ies) of the target sequence may exist in the genome). For example, the target nucleotide sequence may be located at a unique site within the genome of the organism. Target nucleotide sequences may be, for example and without limitation, randomly dispersed throughout the genome with respect to one another; located in different linkage groups in the genome; located in the same linkage group; located on different chromosomes; located on the same chromosome; located in the genome at sites that are expressed under similar conditions in the organism (e.g., under the control of the same, or substantially functionally identical, regulatory factors); and located closely to one another in the genome (e.g., target sequences may be comprised within nucleic acids integrated as concatemers at genomic loci).

Targeting Endonucleases

In particular embodiments, a DNA-binding polypeptide that specifically recognizes and binds to a target nucleotide sequence may be comprised within a chimeric polypeptide, so as to confer specific binding to the target sequence upon the chimeric polypeptide. In examples, such a chimeric polypeptide may comprise, for example and without limitation, nuclease, recombinase, and/or ligase polypeptides, as these polypeptides are described above. Chimeric polypeptides comprising a DNA-binding polypeptide and a nuclease, recombinase, and/or ligase polypeptide may also comprise other functional polypeptide motifs and/or domains, such as for example and without limitation: a spacer sequence positioned between the functional polypeptides in the chimeric protein; a leader peptide; a peptide that targets the fusion protein to an organelle (e.g., the nucleus); polypeptides that are cleaved by a cellular enzyme; peptide tags (e.g., Myc, His, etc.); and other amino acid sequences that do not interfere with the function of the chimeric polypeptide.

Functional polypeptides (e.g., DNA-binding polypeptides and nuclease polypeptides) in a chimeric polypeptide may be operatively linked. In some embodiments, functional polypeptides of a chimeric polypeptide may be operatively linked by their expression from a single polynucleotide encoding at least the functional polypeptides ligated to each other in-frame, so as to create a chimeric gene encoding a chimeric protein. In alternative embodiments, the functional polypeptides of a chimeric polypeptide may be operatively linked by other means, such as by cross-linkage of independently expressed polypeptides.

In some embodiments, a DNA-binding polypeptide, or guide RNA that specifically recognizes and binds to a target nucleotide sequence may be comprised within a natural isolated protein (or mutant thereof), wherein the natural isolated protein or mutant thereof also comprises a nuclease polypeptide (and may also comprise a recombinase and/or ligase polypeptide). Examples of such isolated proteins include TALENs, recombinases (e.g., Cre, Hin, Tre, and FLP recombinase), CRISPR systems, and meganucleases.

As used herein, the term "targeting endonuclease" refers to natural or engineered isolated proteins and mutants thereof that comprise a DNA-binding polypeptide or guide RNA and a nuclease polypeptide, as well as to chimeric polypeptides comprising a DNA-binding polypeptide or guide RNA and a nuclease. Any targeting endonuclease comprising a DNA-binding polypeptide or guide RNA that specifically recognizes and binds to a target nucleotide sequence comprised within a SSTR locus (e.g., either because the target sequence is comprised within the native sequence at the locus, or because the target sequence has been introduced into the locus, for example, by recombination) may be utilized in certain embodiments.

Some examples of chimeric polypeptides that may be useful in particular embodiments of the invention include, without limitation, combinations of the following polypeptides: zinc finger DNA-binding polypeptides; a FokI nuclease polypeptide; TALE domains; leucine zippers; transcription factor DNA-binding motifs; and DNA recognition and/or cleavage domains isolated from, for example and without limitation, a TALEN, a recombinase (e.g., Cre, Hin, RecA, Tre, and FLP recombinases), a CRISPR system, a meganuclease; and others known to those in the art. Particular examples include a chimeric protein comprising a site-specific DNA binding polypeptide and a nuclease polypeptide. Chimeric polypeptides may be engineered by methods known to those of skill in the art to alter the recognition sequence of a DNA-binding polypeptide comprised within the chimeric polypeptide, so as to target the chimeric polypeptide to a particular nucleotide sequence of interest.

In certain embodiments, the chimeric polypeptide comprises a DNA-binding domain (e.g., zinc finger, TAL-effector domain, etc.) and a nuclease (cleavage) domain. The cleavage domain may be heterologous to the DNA-binding domain, for example a zinc finger DNA-binding domain and a cleavage domain from a nuclease or a TALEN DNA-binding domain and a cleavage domain, or meganuclease DNA-binding domain and cleavage domain from a different nuclease. Heterologous cleavage domains can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) Nucleic Acids Res. 25:3379-3388. Additional enzymes which cleave DNA are known (e.g., 51 Nuclease; mung bean nuclease; pancreatic DNase I; micrococcal nuclease; yeast HO endonuclease; see also Linn et al. (eds.) Nucleases, Cold Spring Harbor Laboratory Press, 1993). One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides, or nucleotide pairs, can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding, for example, such that one or more exogenous sequences (donors/transgenes) are integrated at or near the binding (target) sites. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) Proc. Natl. Acad. Sci. USA 89:4275-4279; Li et al. (1993) Proc. Natl. Acad. Sci. USA 90:2764-2768; Kim et al. (1994a) Proc. Natl. Acad. Sci. USA 91:883-887; Kim et al. (1994b) J. Biol. Chem. 269: 31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is Fok I. This particular enzyme is active as a dimer. Bitinaite et al. (1998) Proc. Natl. Acad. Sci. USA 95: 10,570-10,575. Accordingly, for the purposes of the present disclosure, the portion of the Fok I enzyme used in the disclosed fusion proteins is considered a cleavage half-domain. Thus, for targeted double-stranded cleavage and/or targeted replacement of cellular sequences using zinc finger-Fok I fusions, two fusion proteins, each comprising a FokI cleavage half-domain, can be used to reconstitute a catalytically active cleavage domain. Alternatively, a single polypeptide molecule containing a DNA binding domain and two Fok I cleavage half-domains can also be used.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in U.S. Patent Publication No. 20070134796, incorporated herein in its entirety. Additional restriction enzymes also contain separable binding and cleavage domains, and these are contemplated by the present disclosure. See, for example, Roberts et al. (2003) Nucleic Acids Res. 31:418-420.

In certain embodiments, the cleavage domain comprises one or more engineered cleavage half-domain (also referred to as dimerization domain mutants) that minimize or prevent homodimerization, as described, for example, in U.S. Patent Publication Nos. 20050064474; 20060188987 and 20080131962, the disclosures of all of which are incorporated by reference in their entireties herein.

Alternatively, nucleases may be assembled in vivo at the nucleic acid target site using so-called "split-enzyme" technology (see e.g. U.S. Patent Publication No. 20090068164). Components of such split enzymes may be expressed either on separate expression constructs, or can be linked in one open reading frame where the individual components are separated, for example, by a self-cleaving 2A peptide or IRES sequence. Components may be individual zinc finger binding domains or domains of a meganuclease nucleic acid binding domain.

Zinc Finger Nucleases

In some embodiments, a chimeric polypeptide is a custom-designed zinc finger nuclease (ZFN) that may be designed to deliver a targeted site-specific double-strand DNA break into which an exogenous nucleic acid, or donor DNA, may be integrated (See US Patent publication 20100257638, incorporated by reference herein). ZFNs are chimeric polypeptides containing a non-specific cleavage domain from a restriction endonuclease (for example, FokI) and a zinc finger DNA-binding domain polypeptide. See, e.g., Huang et al. (1996) J. Protein Chem. 15:481-9; Kim et al. (1997a) Proc. Natl. Acad. Sci. USA 94:3616-20; Kim et al. (1996) Proc. Natl. Acad. Sci. USA 93:1156-60; Kim et al. (1994) Proc Natl. Acad. Sci. USA 91:883-7; Kim et al. (1997b) Proc. Natl. Acad. Sci. USA 94:12875-9; Kim et al. (1997c) Gene 203:43-9; Kim et al. (1998) Biol. Chem. 379:489-95; Nahon and Raveh (1998) Nucleic Acids Res. 26:1233-9; Smith et al. (1999) Nucleic Acids Res. 27:674-81. In some embodiments, the ZFNs comprise non-canonical zinc finger DNA binding domains (see US Patent publication 20080182332, incorporated by reference herein). The FokI restriction endonuclease must dimerize via the nuclease domain in order to cleave DNA and introduce a double-strand break. Consequently, ZFNs containing a nuclease domain from such an endonuclease also require dimerization of the nuclease domain in order to cleave target DNA. Mani et al. (2005) Biochem. Biophys. Res. Commun. 334:1191-7; Smith et al. (2000) Nucleic Acids Res. 28:3361-9. Dimerization of the ZFN can be facilitated by two adjacent, oppositely oriented DNA-binding sites. Id.

In some embodiments, a method for the site-specific integration of an exogenous nucleic acid into at least one SSTR locus of a host comprises introducing into a cell of the host a ZFN, wherein the ZFN recognizes and binds to a target nucleotide sequence, wherein the target nucleotide sequence is comprised within at least one SSTR locus of the host. In certain examples, the target nucleotide sequence is not comprised within the genome of the host at any other position than the at least one SSTR locus. For example, a DNA-binding polypeptide of the ZFN may be engineered to recognize and bind to a target nucleotide sequence identified within the at least one SSTR locus (e.g., by sequencing the SSTR locus). A method for the site-specific integration of an exogenous nucleic acid into at least one SSTR locus of a host that comprises introducing into a cell of the host a ZFN may also comprise introducing into the cell an exogenous nucleic acid, wherein recombination of the exogenous nucleic acid into a nucleic acid of the host comprising the at least one SSTR locus is facilitated by site-specific recognition and binding of the ZFN to the target sequence (and subsequent cleavage of the nucleic acid comprising the SSTR locus).

Optional Exogenous Nucleic Acids for Integration at a SSTR Locus

Embodiments of the invention may include one or more nucleic acids selected from the group consisting of: an exogenous nucleic acid for site-specific integration in at least one SSTR locus, for example and without limitation, an ORF; a nucleic acid comprising a nucleotide sequence encoding a targeting endonuclease; and a vector comprising at least one of either or both of the foregoing. Thus, particular nucleic acids for use in some embodiments include nucleotide sequences encoding a polypeptide, structural nucleotide sequences, and/or DNA-binding polypeptide recognition and binding sites.

Optional Exogenous Nucleic Acid Molecules for Site-Specific Integration

As noted above, insertion of an exogenous sequence (also called a "donor sequence" or "donor" or "transgene") is provided, for example for expression of a polypeptide, correction of a mutant gene or for increased expression of a wild-type gene. It will be readily apparent that the donor sequence is typically not identical to the genomic sequence where it is placed. A donor sequence can contain a non-homologous sequence flanked by two regions of homology to allow for efficient HDR at the location of interest. Additionally, donor sequences can comprise a vector molecule containing sequences that are not homologous to the region of interest in cellular chromatin. A donor molecule can contain several, discontinuous regions of homology to cellular chromatin. For example, for targeted insertion of sequences not normally present in a region of interest, said sequences can be present in a donor nucleic acid molecule and flanked by regions of homology to sequence in the region of interest.

The donor polynucleotide can be DNA or RNA, single-stranded or double-stranded and can be introduced into a cell in linear or circular form. See e.g., U.S. Patent Publication Nos. 20100047805, 20110281361, 20110207221 and U.S. application Ser. No. 13/889,162. If introduced in linear form, the ends of the donor sequence can be protected (e.g. from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al. (1987) Proc. Natl. Acad. Sci. USA 84:4959-4963; Nehls et al. (1996) Science 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

A polynucleotide can be introduced into a cell as part of a vector molecule having additional sequences such as, for example, replication origins, promoters and genes encoding antibiotic resistance. Moreover, donor polynucleotides can be introduced as naked nucleic acid, as nucleic acid complexed with an agent such as a liposome or poloxamer, or can be delivered by viruses (e.g., adenovirus, AAV, herpesvirus, retrovirus, lentivirus and integrase defective lentivirus (IDLV)).

The donor is generally integrated so that its expression is driven by the endogenous promoter at the integration site, namely the promoter that drives expression of the endogenous gene into which the donor is integrated (e.g., SSTR). However, it will be apparent that the donor may comprise a promoter and/or enhancer, for example a constitutive promoter or an inducible or tissue specific promoter.

Furthermore, although not required for expression, exogenous sequences may also include transcriptional or translational regulatory sequences, for example, promoters, enhancers, insulators, internal ribosome entry sites, sequences encoding 2A peptides and/or polyadenylation signals.

Exogenous nucleic acids that may be integrated in a site-specific manner into at least one SSTR locus, so as to modify the SSTR locus, in embodiments include, for example and without limitation, nucleic acids comprising a nucleotide sequence encoding a polypeptide of interest; nucleic acids comprising an agronomic gene; nucleic acids comprising a nucleotide sequence encoding an RNAi molecule; or nucleic acids that disrupt the SSTR gene.

In some embodiments, an exogenous nucleic acid is integrated at a SSTR locus, so as to modify the SSTR locus, wherein the nucleic acid comprises a nucleotide sequence encoding a polypeptide of interest, such that the nucleotide sequence is expressed in the host from the SSTR locus. In some examples, the polypeptide of interest (e.g., a foreign protein) is expressed from a nucleotide sequence encoding the polypeptide of interest in commercial quantities. In such examples, the polypeptide of interest may be extracted from the host cell, tissue, or biomass.

Nucleic Acid Molecules Comprising a Nucleotide Sequence Encoding a Targeting Endonuclease In some embodiments, a nucleotide sequence encoding a targeting endonuclease may be engineered by manipulation (e.g., ligation) of native nucleotide sequences encoding polypeptides comprised within the targeting endonuclease. For example, the nucleotide sequence of a gene encoding a protein comprising a DNA-binding polypeptide may be inspected to identify the nucleotide sequence of the gene that corresponds to the DNA-binding polypeptide, and that nucleotide sequence may be used as an element of a nucleotide sequence encoding a targeting endonuclease comprising the DNA-binding polypeptide. Alternatively, the amino acid sequence of a targeting endonuclease may be used to deduce a nucleotide sequence encoding the targeting endonuclease, for example, according to the degeneracy of the genetic code.

In exemplary nucleic acid molecules comprising a nucleotide sequence encoding a targeting endonuclease, the last codon of a first polynucleotide sequence encoding a nuclease polypeptide, and the first codon of a second polynucleotide sequence encoding a DNA-binding polypeptide, may be separated by any number of nucleotide triplets, e.g., without coding for an intron or a "STOP." Likewise, the last codon of a nucleotide sequence encoding a first polynucleotide sequence encoding a DNA-binding polypeptide, and the first codon of a second polynucleotide sequence encoding a nuclease polypeptide, may be separated by any number of nucleotide triplets. In these and further embodiments, the last codon of the last (i.e., most 3' in the nucleic acid sequence) of a first polynucleotide sequence encoding a nuclease polypeptide, and a second polynucleotide sequence encoding a DNA-binding polypeptide, may be fused in phase-register with the first codon of a further polynucleotide coding sequence directly contiguous thereto, or separated therefrom by no more than a short peptide sequence, such as that encoded by a synthetic nucleotide linker (e.g., a nucleotide linker that may have been used to achieve the fusion). Examples of such further polynucleotide sequences include, for example and without limitation, tags, targeting peptides, and enzymatic cleavage sites. Likewise, the first codon of the most 5' (in the nucleic acid sequence) of the first and second polynucleotide sequences may be fused in phase-register with the last codon of a further polynucleotide coding sequence directly contiguous thereto, or separated therefrom by no more than a short peptide sequence.

A sequence separating polynucleotide sequences encoding functional polypeptides in a targeting endonuclease (e.g., a DNA-binding polypeptide and a nuclease polypeptide) may, for example, consist of any sequence, such that the amino acid sequence encoded is not likely to significantly alter the translation of the targeting endonuclease. Due to the autonomous nature of known nuclease polypeptides and known DNA-binding polypeptides, intervening sequences will not in examples interfere with the respective functions of these structures.

Other Knockout Methods

Various other techniques known in the art can be used to inactivate genes to make knock-out animals and/or to introduce nucleic acid constructs into animals to produce founder animals and to make animal lines, in which the knockout or nucleic acid construct is integrated into the genome. Such techniques include, without limitation, pronuclear microinjection (U.S. Pat. No. 4,873,191), retrovirus mediated gene transfer into germ lines (Van der Putten et al. (1985) Proc. Natl. Acad. Sci. USA 82, 6148-1652), gene targeting into embryonic stem cells (Thompson et al. (1989) Cell 56, 313-321), electroporation of embryos (Lo (1983) Mol. Cell. Biol. 3, 1803-1814), sperm-mediated gene transfer (Lavitrano et al. (2002) Proc. Natl. Acad. Sci. USA 99, 14230-14235; Lavitrano et al. (2006) Reprod. Fert. Develop. 18, 19-23), and in vitro transformation of somatic cells, such as cumulus or mammary cells, or adult, fetal, or embryonic stem cells, followed by nuclear transplantation (Wilmut et al. (1997) Nature 385, 810-813; and Wakayama et al. (1998) Nature 394, 369-374). Pronuclear microinjection, sperm mediated gene transfer, and somatic cell nuclear transfer are particularly useful techniques. An animal that is genomically modified is an animal wherein all of its cells have the genetic modification, including its germ line cells. When methods are used that produce an animal that is mosaic in its genetic modification, the animals may be inbred and progeny that are genomically modified may be selected. Cloning, for instance, may be used to make a mosaic animal if its cells are modified at the blastocyst state, or genomic modification can take place when a single-cell is modified. If a particular gene is inactivated by a knock out modification, homozygosity would normally be required. If a particular gene is inactivated by an RNA interference or dominant negative strategy, then heterozygosity is often adequate.

Typically, in embryo/zygote microinjection, a nucleic acid construct or mRNA is introduced into a fertilized egg; 1 or 2 cell fertilized eggs are used as the pronuclei containing the genetic material from the sperm head and the egg are visible within the protoplasm. Pronuclear staged fertilized eggs can be obtained in vitro or in vivo (i.e., surgically recovered from the oviduct of donor animals). In vitro fertilized eggs can be produced as follows. For example, swine ovaries can be collected at an abattoir, and maintained at 22-28° C. during transport. Ovaries can be washed and isolated for follicular aspiration, and follicles ranging from 4-8 mm can be aspirated into 50 mL conical centrifuge tubes using 18 gauge needles and under vacuum. Follicular fluid and aspirated oocytes can be rinsed through pre-filters with commercial TL-HEPES (Minitube, Verona, Wis.). Oocytes surrounded by a compact cumulus mass can be selected and placed into TCM-199 OOCYTE MATURATION MEDIUM (Minitube) supplemented with 0.1 mg/mL cysteine, 10 ng/mL epidermal growth factor, 10% porcine follicular fluid, 50 µM 2-mercaptoethanol, 0.5 mg/ml cAMP, 10 IU/mL each of pregnant mare serum gonadotropin (PMSG) and human chorionic gonadotropin (hCG) for approximately 22 hours in humidified air at 38.7° C. and 5% $CO_2$. Subsequently, the oocytes can be moved to fresh TCM-199 maturation medium, which will not contain cAMP, PMSG or hCG and incubated for an additional 22 hours. Matured oocytes can be stripped of their cumulus cells by vortexing in 0.10% hyaluronidase for 1 minute.

For swine, mature oocytes can be fertilized in 500 µl Minitube PORCPRO IVF MEDIUM SYSTEM (Minitube) in Minitube 5-well fertilization dishes. In preparation for in vitro fertilization (IVF), freshly-collected or frozen boar semen can be washed and resuspended in PORCPRO IVF Medium to 4×10×5 sperm. Sperm concentrations can be analyzed by computer assisted semen analysis (SPERMVISION, Minitube). Final in vitro insemination can be performed in a 10 µl volume at a final concentration of approximately 40 motile sperm/oocyte, depending on boar. Incubate all fertilizing oocytes at 38.7° C. in 5.0% $CO_2$ atmosphere for 6 hours. Six hours post-insemination, presumptive zygotes can be washed twice in NCSU-23 and moved to 0.5 mL of the same medium. This system can produce 20-30% blastocysts routinely across most boars with a 10-30% polyspermic insemination rate.

Linearized nucleic acid constructs or mRNA can be injected into one of the pronuclei or into the cytoplasm. Then the injected eggs can be transferred to a recipient female (e.g., into the oviducts of a recipient female) and allowed to develop in the recipient female to produce the transgenic animals. In particular, in vitro fertilized embryos can be centrifuged at 15,000×g for 5 minutes to sediment lipids allowing visualization of the pronucleus. The embryos can be injected with using an Eppendorf FEMTOJET injector and can be cultured until blastocyst formation. Rates of embryo cleavage and blastocyst formation and quality can be recorded.

Embryos can be surgically transferred into uteri of asynchronous recipients. Typically, 100-200 (e.g., 150-200) embryos can be deposited into the ampulla-isthmus junction of the oviduct using a 5.5-inch TOMCAT® catheter. After surgery, real-time ultrasound examination of pregnancy can be performed.

In somatic cell nuclear transfer, a transgenic cell (e.g., a transgenic pig cell or bovine cell) such as an embryonic blastomere, fetal fibroblast, adult ear fibroblast, or granulosa cell that includes a nucleic acid construct described above, can be introduced into an enucleated oocyte to establish a combined cell. Oocytes can be enucleated by partial zona dissection near the polar body and then pressing out cytoplasm at the dissection area. Typically, an injection pipette with a sharp beveled tip is used to inject the transgenic cell into an enucleated oocyte arrested at meiosis 2. In some conventions, oocytes arrested at meiosis-2 are termed eggs. After producing a porcine or bovine embryo (e.g., by fusing and activating the oocyte), the embryo is transferred to the oviducts of a recipient female, about 20 to 24 hours after activation. See, for example, Cibelli et al. (1998) Science 280, 1256-1258 and U.S. Pat. No. 6,548,741. For pigs, recipient females can be checked for pregnancy approximately 20-21 days after transfer of the embryos.

Standard breeding techniques can be used to create animals that are homozygous for the edited nucleic acid from the initial heterozygous founder animals. Homozygosity may not be required, however. Transgenic pigs described herein can be bred with other pigs of interest.

Once transgenic animals have been generated, presence of the edited nucleic acid can be assessed using standard techniques. Initial screening can be accomplished by sequencing or Southern blot analysis. For a description of Southern analysis, see sections 9.37-9.52 of Sambrook et al., 1989, Molecular Cloning, A Laboratory Manual, second edition, Cold Spring Harbor Press, Plainview; N.Y. Polymerase chain reaction (PCR) techniques also can be used in the initial screening. PCR refers to a procedure or technique in which target nucleic acids are amplified. Generally, sequence information from the ends of the region of interest or beyond are employed to design oligonucleotide primers that are identical or similar in sequence to opposite strands of the template to be amplified. PCR can be used to amplify specific sequences from DNA as well as RNA, including sequences from total genomic DNA or total cellular RNA. Primers typically are 14 to 40 nucleotides in length, but can range from 10 nucleotides to hundreds of nucleotides in length. PCR is described in, for example PCR Primer: A Laboratory Manual, ed. Dieffenbach and Dveksler, Cold Spring Harbor Laboratory Press, 1995. Nucleic acids also can be amplified by ligase chain reaction, strand displacement amplification, self-sustained sequence replication, or nucleic acid sequence-based amplified. See, for example, Lewis (1992) Genetic Engineering News 12,1; Guatelli et al. (1990) Proc. Natl. Acad. Sci. USA 87:1874; and Weiss (1991) Science 254:1292. At the blastocyst stage, embryos can be individually processed for analysis by PCR, Southern hybridization and splinkerette PCR (see, e.g., Dupuy et al. Proc Natl Acad Sci USA (2002) 99:4495).

Expression of a nucleic acid sequence encoding a polypeptide in the tissues of transgenic pigs can be assessed using techniques that include, for example, Northern blot analysis of tissue samples obtained from the animal, in situ hybridization analysis, Western analysis, immunoassays such as enzyme-linked immunosorbent assays, and reverse-transcriptase PCR (RT-PCR).

Interfering RNAs

A variety of interfering RNA (RNAi) systems are known. Double-stranded RNA (dsRNA) induces sequence-specific degradation of homologous gene transcripts. RNA-induced silencing complex (RISC) metabolizes dsRNA to small 21-23-nucleotide small interfering RNAs (siRNAs). RISC contains a double stranded RNAse (dsRNase, e.g., Dicer) and ssRNase (e.g., Argonaut 2 or Ago2). RISC utilizes antisense strand as a guide to find a cleavable target. Both siRNAs and microRNAs (miRNAs) are known. A method of inactivating a gene in a genetically edited animal comprises inducing RNA interference against a target gene and/or nucleic acid such that expression of the target gene and/or nucleic acid is reduced.

For example, the exogenous nucleic acid sequence can induce RNA interference against a nucleic acid encoding a polypeptide. For example, double-stranded small interfering RNA (siRNA) or small hairpin RNA (shRNA) homologous to a target DNA can be used to reduce expression of that DNA. Constructs for siRNA can be produced as described, for example, in Fire et al. (1998) Nature 391:806; Romano and Masino (1992) Mol. Microbiol. 6:3343; Cogoni et al. (1996) EMBO J. 15:3153; Cogoni and Masino (1999) Nature 399:166; Misquitta and Paterson (1999) Proc. Natl. Acad. Sci. USA 96:1451; and Kennerdell and Carthew (1998) Cell 95:1017. Constructs for shRNA can be produced as described by McIntyre and Fanning (2006) BMC Biotechnology 6:1. In general, shRNAs are transcribed as a single-stranded RNA molecule containing complementary regions, which can anneal and form short hairpins.

The probability of finding a single, individual functional siRNA or miRNA directed to a specific gene is high. The predictability of a specific sequence of siRNA, for instance, is about 50% but a number of interfering RNAs may be made with good confidence that at least one of them will be effective.

Embodiments include an in vitro cell, an in vivo cell, and a genetically edited animal such as a livestock animal that express an RNAi directed against a somatostatin receptor gene selective for improved growth performance. An embodiment is an RNAi directed against a gene selected from SSTR1, SSTR2, SSTR3, SSTR4, and SSTR5. The RNAi may be, for instance, selected from the group consisting of siRNA, shRNA, dsRNA, RISC and miRNA.

Inducible Systems

An inducible system may be used to control expression of a somatostatin receptor gene. Various inducible systems are known that allow spatiotemporal control of expression of a gene. Several have been proven to be functional in vivo in transgenic animals.

An example of an inducible system is the tetracycline (tet)-on promoter system, which can be used to regulate transcription of the nucleic acid. In this system, a mutated Tet repressor (TetR) is fused to the activation domain of herpes simplex virus VP 16 transactivator protein to create a tetracycline-controlled transcriptional activator (tTA), which is regulated by tet or doxycycline (dox). In the absence of antibiotic, transcription is minimal, while in the presence of tet or dox, transcription is induced. Alternative inducible systems include the ecdysone or rapamycin systems. Ecdysone is an insect molting hormone whose production is controlled by a heterodimer of the ecdysone receptor and the product of the ultraspiracle gene (USP). Expression is induced by treatment with ecdysone or an analog of ecdysone such as muristerone A. The agent that is administered to the animal to trigger the inducible system is referred to as an induction agent.

The tetracycline-inducible system and the Cre/loxP recombinase system (either constitutive or inducible) are among the more commonly used inducible systems. The tetracycline-inducible system involves a tetracycline-controlled transactivator (tTA)/reverse tTA (rtTA). A method to use these systems in vivo involves generating two lines of genetically edited animals. One animal line expresses the activator (tTA, rtTA, or Cre recombinase) under the control of a selected promoter. Another set of transgenic animals express the acceptor, in which the expression of the gene of interest (or the gene to be modified) is under the control of the target sequence for the tTA/rtTA transactivators (or is flanked by loxP sequences). Mating the two strains of mice provides control of gene expression.

The tetracycline-dependent regulatory systems (tet systems) rely on two components, i.e., a tetracycline-controlled transactivator (tTA or rtTA) and a tTA/rtTA-dependent promoter that controls expression of a downstream cDNA, in a tetracycline-dependent manner. In the absence of tetracycline or its derivatives (such as doxycycline), tTA binds to tetO sequences, allowing transcriptional activation of the tTA-dependent promoter. However, in the presence of doxycycline, tTA cannot interact with its target and transcription does not occur. The tet system that uses tTA is termed tet-OFF, because tetracycline or doxycycline allows transcriptional down-regulation. Administration of tetracycline or its derivatives allows temporal control of transgene expression in vivo. rtTA is a variant of tTA that is not functional in the absence of doxycycline but requires the presence of the ligand for transactivation. This tet system is therefore termed tet-ON. The tet systems have been used in vivo for the inducible expression of several transgenes, encoding, e.g., reporter genes, oncogenes, or proteins involved in a signaling cascade.

The Cre/lox system uses the Cre recombinase, which catalyzes site-specific recombination by crossover between two distant Cre recognition sequences, i.e., loxP sites. A DNA sequence introduced between the two loxP sequences (termed foxed DNA) is excised by Cre-mediated recombination. Control of Cre expression in a transgenic animal, using either spatial control (with a tissue- or cell-specific promoter), or temporal control (with an inducible system), results in control of DNA excision between the two loxP sites. One application is for conditional gene inactivation (conditional knockout). Another approach is for protein over-expression, wherein a foxed stop codon is inserted between the promoter sequence and the DNA of interest. Genetically edited animals do not express the transgene until Cre is expressed, leading to excision of the floxed stop codon. This system has been applied to tissue-specific oncogenesis and controlled antigene receptor expression in B lymphocytes. Inducible Cre recombinases have also been developed. The inducible Cre recombinase is activated only by administration of an exogenous ligand. The inducible Cre recombinases are fusion proteins containing the original Cre recombinase and a specific ligand-binding domain. The functional activity of the Cre recombinase is dependent on an external ligand that is able to bind to this specific domain in the fusion protein.

Embodiments include an in vitro cell, an in vivo cell, and a genetically edited animal such as a livestock animal that comprise a somatostatin receptor gene selective for improved growth performance that is under control of an inducible system. The genetic modification of an animal may be genomic or mosaic. An embodiment is a gene in the group consisting of SSTR1, SSTR2, SSTR3, SSTR4, and SSTR5 that is under control of an inducible system. The inducible system may be, for instance, selected from the group consisting of Tet-On, Tet-Off, Cre-lox, and Hif1 alpha.

Vectors and Nucleic Acids

A variety of nucleic acids may be introduced into cells for knockout purposes, for inactivation of a gene, to obtain expression of a gene, or for other purposes. As used herein, the term nucleic acid includes DNA, RNA, and nucleic acid analogs, and nucleic acids that are double-stranded or single-stranded (i.e., a sense or an antisense single strand). Nucleic acid analogs can be modified at the base moiety, sugar moiety, or phosphate backbone to improve, for example, stability, hybridization, or solubility of the nucleic acid. Modifications at the base moiety include deoxyuridine for deoxythymidine, and 5-methyl-2'-deoxycytidine and 5-bromo-2'-doxycytidine for deoxycytidine. Modifications of the sugar moiety include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six membered, morpholino ring, or peptide nucleic acids, in which the deoxyphosphate backbone is replaced by a pseudopeptide backbone and the four bases are retained. See, Summerton and Weller (1997) Antisense Nucleic Acid Drug Dev. 7(3):187; and Hyrup et al. (1996) Bioorgan. Med. Chem. 4:5. In addition, the deoxyphosphate backbone can be replaced with, for example, a phosphorothioate or phosphorodithioate backbone, a phosphoroamidite, or an alkyl phosphotriester backbone.

The target nucleic acid sequence can be operably linked to a regulatory region such as a promoter. Regulatory regions can be porcine regulatory regions or can be from other species. As used herein, operably linked refers to positioning of a regulatory region relative to a nucleic acid sequence in such a way as to permit or facilitate transcription of the target nucleic acid.

Any type of promoter can be operably linked to a target nucleic acid sequence. Examples of promoters include, without limitation, tissue-specific promoters, constitutive promoters, inducible promoters, and promoters responsive or unresponsive to a particular stimulus. Suitable tissue specific promoters can result in preferential expression of a nucleic acid transcript in beta cells and include, for example, the human insulin promoter. Other tissue specific promoters can result in preferential expression in, for example, hepatocytes or heart tissue and can include the albumin or alpha-myosin heavy chain promoters, respectively. In other embodiments, a promoter that facilitates the expression of a nucleic acid molecule without significant tissue or temporal-specificity can be used (i.e., a constitutive promoter). For example, a beta-actin promoter such as the chicken beta-actin gene promoter, ubiquitin promoter, miniCAGs promoter, glyceraldehyde-3-phosphate dehydrogenase (GAPDH) promoter, or 3-phosphoglycerate kinase (PGK) promoter can be used, as well as viral promoters such as the herpes simplex virus thymidine kinase (HSV-TK) promoter, the SV40 promoter, or a cytomegalovirus (CMV) promoter. In some embodiments, a fusion of the chicken beta actin gene promoter and the CMV enhancer is used as a promoter. See, for example, Xu et al. (2001) Hum. Gene Ther. 12:563; and Kiwaki et al. (1996) Hum. Gene Ther. 7:821.

Additional regulatory regions that may be useful in nucleic acid constructs, include, but are not limited to, polyadenylation sequences, translation control sequences (e.g., an internal ribosome entry segment, IRES), enhancers, inducible elements, or introns. Such regulatory regions may not be necessary, although they may increase expression by affecting transcription, stability of the mRNA, translational efficiency, or the like. Such regulatory regions can be included in a nucleic acid construct as desired to obtain optimal expression of the nucleic acids in the cell(s). Sufficient expression, however, can sometimes be obtained without such additional elements.

A nucleic acid construct may be used that encodes signal peptides or selectable markers. Signal peptides can be used such that an encoded polypeptide is directed to a particular cellular location (e.g., the cell surface). Non-limiting examples of selectable markers include puromycin, ganciclovir, adenosine deaminase (ADA), aminoglycoside phosphotransferase (neo, G418, APH), dihydrofolate reductase (DHFR), hygromycin-B-phosphtransferase, thymidine kinase (TK), and xanthin-guanine phosphoribosyltransferase (XGPRT). Such markers are useful for selecting stable transformants in culture. Other selectable markers include fluorescent polypeptides, such as green fluorescent protein or yellow fluorescent protein.

In some embodiments, a sequence encoding a selectable marker can be flanked by recognition sequences for a recombinase such as, e.g., Cre or Flp. For example, the selectable marker can be flanked by loxP recognition sites (34-bp recognition sites recognized by the Cre recombinase) or FRT recognition sites such that the selectable marker can be excised from the construct. See, Orban, et al., Proc. Natl. Acad. Sci. (1992) 89:6861, for a review of Cre/lox technology, and Brand and Dymecki, Dev. Cell (2004) 6:7. A transposon containing a Cre- or Flp-activatable transgene interrupted by a selectable marker gene also can be used to obtain transgenic animals with conditional expression of a transgene. For example, a promoter driving expression of the marker/transgene can be either ubiquitous or tissue-specific, which would result in the ubiquitous or tissue-specific expression of the marker in F0 animals (e.g., pigs). Tissue specific activation of the transgene can be accomplished, for example, by crossing a pig that ubiquitously expresses a marker-interrupted transgene to a pig expressing Cre or Flp in a tissue-specific manner, or by crossing a pig that expresses a marker-interrupted transgene in a tissue-specific manner to a pig that ubiquitously expresses Cre or Flp recombinase. Controlled expression of the transgene or controlled excision of the marker allows expression of the transgene.

In some embodiments, the exogenous nucleic acid encodes a polypeptide. A nucleic acid sequence encoding a polypeptide can include a tag sequence that encodes a "tag" designed to facilitate subsequent manipulation of the encoded polypeptide (e.g., to facilitate localization or detection). Tag sequences can be inserted in the nucleic acid sequence encoding the polypeptide such that the encoded tag is located at either the carboxyl or amino terminus of the polypeptide. Non-limiting examples of encoded tags include glutathione S-transferase (GST) and FLAG™ ag (Kodak, New Haven, Conn.).

Nucleic acid constructs can be methylated using an SssI CpG methylase (New England Biolabs, Ipswich, Mass.). In general, the nucleic acid construct can be incubated with S-adenosylmethionine and SssI CpG-methylase in buffer at 37° C. Hypermethylation can be confirmed by incubating the construct with one unit of HinP1I endonuclease for 1 hour at 37° C. and assaying by agarose gel electrophoresis.

Nucleic acid constructs can be introduced into embryonic, fetal, or adult animal cells of any type, including, for example, germ cells such as an oocyte or an egg, a progenitor cell, an adult or embryonic stem cell, a primordial germ cell, a kidney cell such as a PK-15 cell, an islet cell, a beta cell, a liver cell, or a fibroblast such as a dermal fibroblast, using a variety of techniques. Non-limiting examples of techniques include the use of transposon systems, recombinant viruses that can infect cells, or liposomes or other non-viral methods such as electroporation, microinjection, or calcium phosphate precipitation, that are capable of delivering nucleic acids to cells.

In transposon systems, the transcriptional unit of a nucleic acid construct, i.e., the regulatory region operably linked to an exogenous nucleic acid sequence, is flanked by an inverted repeat of a transposon. Several transposon systems, including, for example, Sleeping Beauty (see, U.S. Pat. No. 6,613,752 and U.S. Publication No. 2005/0003542); Frog Prince (Miskey et al. (2003) Nucleic Acids Res. 31:6873); Tol2 (Kawakami (2007) Genome Biology 8 (Suppl. 1):57; Minos (Pavlopoulos et al. (2007) Genome Biology 8 (Suppl. 1): S2); Hsmar1 (Miskey et al. (2007)) Mol Cell Biol. 27:4589); and Passport have been developed to introduce nucleic acids into cells, including mice, human, and pig cells. The Sleeping Beauty transposon is particularly useful. A transposase can be delivered as a protein, encoded on the same nucleic acid construct as the exogenous nucleic acid, can be introduced on a separate nucleic acid construct, or provided as an mRNA (e.g., an in vitro-transcribed and capped mRNA).

Insulator elements also can be included in a nucleic acid construct to maintain expression of the exogenous nucleic acid and to inhibit the unwanted transcription of host genes. See, for example, U.S. Publication No. 2004/0203158. Typically, an insulator element flanks each side of the transcriptional unit and is internal to the inverted repeat of the transposon. Non-limiting examples of insulator elements include the matrix attachment region-(MAR) type insulator elements and border-type insulator elements. See, for example, U.S. Pat. Nos. 6,395,549, 5,731,178, 6,100,448, and 5,610,053, and U.S. Publication No. 2004/0203158.

Nucleic acids can be incorporated into vectors. A vector is a broad term that includes any specific DNA segment that is designed to move from a carrier into a target DNA. A vector may be referred to as an expression vector, or a vector system, which is a set of components needed to bring about DNA insertion into a genome or other targeted DNA sequence such as an episome, plasmid, or even virus/phage DNA segment. Vector systems such as viral vectors (e.g., retroviruses, adeno-associated virus and integrating phage viruses), and non-viral vectors (e.g., transposons) used for gene delivery in animals have two basic components: 1) a vector comprised of DNA (or RNA that is reverse transcribed into a cDNA) and 2) a transposase, recombinase, or other integrase enzyme that recognizes both the vector and a DNA target sequence and inserts the vector into the target DNA sequence. Vectors most often contain one or more expression cassettes that comprise one or more expression control sequences, wherein an expression control sequence is a DNA sequence that controls and regulates the transcription and/or translation of another DNA sequence or mRNA, respectively.

Many different types of vectors are known. For example, plasmids and viral vectors, e.g., retroviral vectors, are known. Mammalian expression plasmids typically have an origin of replication, a suitable promoter and optional enhancer, necessary ribosome binding sites, a polyadenylation site, splice donor and acceptor sites, transcriptional termination sequences, and 5' flanking non-transcribed sequences. Examples of vectors include: plasmids (which may also be a carrier of another type of vector), adenovirus, adeno-associated virus (AAV), lentivirus (e.g., modified HIV-1, SIV or FIV), retrovirus (e.g., ASV, ALV or MoMLV), and transposons (e.g., Sleeping Beauty, P-elements, To1-2, Frog Prince, piggyBac).

Founder Animals, Animal Lines, Traits, and Reproduction

Founder animals may be produced by cloning and other methods described herein. The founders can be homozygous for a genetic modification, as in the case where a zygote or a primary cell undergoes a homozygous modification. Similarly, founders can also be made that are heterozygous. The founders may be genomically modified, meaning that all of the cells in their genome have undergone modification. Founders can be mosaic for a modification, as may happen when vectors are introduced into one of a plurality of cells in an embryo, typically at a blastocyst stage. Progeny of mosaic animals may be tested to identify progeny that are genomically modified. An animal line is established when a pool of animals has been created that can be reproduced sexually or by assisted reproductive techniques, with heterogeneous or homozygous progeny consistently expressing the modification.

A further embodiment includes a method for screening animals to determine those more likely to exhibit improved growth performance. These methods include obtaining a genetic sample from the animal. The methods can further include assaying for the presence or absence of a modified somatostatin receptor gene associated with improved growth performance.

Further embodiments of the invention can include amplifying the gene or a region of the gene, which contains at least one modification. Since one of the modifications may involve changes in the amino acid composition of the somatostatin receptor protein, assay methods may even involve ascertaining the amino acid composition of these proteins. Methods for this type or purification and analysis typically involve isolation of the protein through means including fluorescence tagging with antibodies, separation and purification of the protein (i.e., through reverse phase HPLC system), and use of an automated protein sequencer to identify the amino acid sequence present. Protocols for this assay are standard and known in the art and are disclosed in Ausubel et al. (eds.), *Short Protocols in Molecular Biology* 4th ed. (John Wiley and Sons 1999).

A further embodiment comprises a breeding method whereby assays of the above types are conducted on a plurality of gene sequences from different animals or animal embryos of various species to be selected from and, based on the results, certain animals are either selected or dropped out of the breeding program.

All references, including publications, patents, and patent applications, cited herein are hereby incorporated by reference to the extent they are not inconsistent with the explicit details of this disclosure, and are so incorporated to the same extent as if each reference were individually and specifically indicated to be incorporated by reference and were set forth in its entirety herein. The references discussed herein are provided solely for their disclosure prior to the filing date of the present application. Nothing herein is to be construed as an admission that the inventors are not entitled to antedate such disclosure by virtue of prior invention. The following examples are provided to illustrate certain particular features and/or embodiments. The examples should not be construed to limit the disclosure to the particular features or embodiments exemplified.

EXAMPLES

Example 1

A surgical embryo transfer, containing somatic cell nuclear transfer and IVF derived embryos that were injected with CRISPR/Cas9 molecules to disrupt the SSTR2 locus (Cas9 mRNA and gRNA that targeted a locus in SSTR2 (SEQ ID NO: 5)), was performed. Two male piglets (74-1 and 74-2) were born alive. Sequencing data (FIGS. 1-3) shows that both pigs are clones resulting from somatic cell nuclear transfer and carry a compound heterozygous mutation with 1 bp or 3 bp deletions in the SSTR2 gene (SEQ ID NOs: 3 and 4). Body weights for 74-1 are above average and 74-2 are well above average for normal piglet growth during lactation (FIG. 4).

Wild Type *Sus scrofa* SSTR2 Nucleotide Sequence (SEQ ID NO: 1)
atggatatggcgtatgagctactcaacgggagccagccgtggctttcctctccat-tcgacctcaat ggctccgtggcaacagccaacagttcaaaccagacggagcat-actatgacctgaccagcaatgca gtcctcacgttcatatattttgtggtctgcatcat-tggcctgtgcggcaacacgcttgtcatttac
gtcatcctccgctacgccaagatgaagacaatcaccaacatctacatcct-caacctggccattgcc gatgagctcttcatgctgggcctgcccttcctggc-catgcaggtggctctggtccactggcccttt ggcaaggccatctgccgggtggt-catgactgtggatggcatcaatcagttcaccagcattttctgc
ttgaccgtcatgagcattgaccggtacctggctgtggtccacccca tcaagtcggc-caagtggagg agaccccggacagccaagatgat-caatgtggccgtgtggggcgtctctctgctggtcatcttgccc atcatga-tatatgccgggcttcgaagcaaccagtggggagaagcagctgcaccatcaac
tggcca ggcgagtcgggggcatggtacacgggggttcattatctacgcctt-catcctgggggttcctggtgccc ctcaccatcatctgtctttgctacctgttcattat-catcaaggtgaagtcctccggaatccgagtg ggttcctccaagaggaaaaagtct-gagaagaaggtcacccggatggtgtccattgtggtggccgtc ttcatttctgctggctcccccttctacatcttcaatgtctcttcggtctctgtggc-catcagtccc accccagccccttaaaggcatgtttgactttgtggtggtcctcacc-tatgctaacagctgtgccaac cctatcctctatgccttcttgtccgacaactt-caagaagagcttccagaatgtcctctgcttggtc
aaggtgagcggcacagatgatggggaacg-gagtgacagtaagcaggacaaatcgcggctgaatgag accacgga-gacccagaggaccctcctcaatggagacctccagaccagtatctga Wild Type *Sus scrofa* SSTR2 Protein Sequence (SEQ ID NO: 2)
MDMAYELLNGSQPWLSSPFDLNGSVA-TANSSNQTEPYYDLTSNAVLTFIYFVVCI-IGLCGNTLVIY VILRYAKMKTITNIYILNLAIA-DELFMLGLPFLAMQVALVHWPFGKAICRVVMTVDG INQFTSIFC LTVMSIDRYLAVVHPIKSAKWRRPRTAK-MINVAVWGVSLLVILPIMIYAGLRSNQWGRSSCT-INWP GESGAWYTGFIIYAFILGFLVPLTIICL-CYLFIIIKVKSSGIRVGSSKRKKSEKKVTRMVSIVVAV FIFCWLPFYIFNVSSVSVAISPTPALKGMFDFVVVLTY-ANSCANPILYAFLSDNFKKSFQNVLCLV KVSGTDDG-ERSDSKQDKSRLNETTETQRTLLNGDLQTSI Modified *Sus scrofa* SSTR2 Nucleotide Sequence (SEQ ID NO: 3) atggatatggcgtatgagctaaacgggagccagccgtggctttcctctc-cattcgacctcaatggc tccgtggcaacagccaacagttcaaaccagacggagc-catactatgacctgaccagcaatgcagtc ctcacgttcatatattttgtggtctgcat-cattggcctgtgcggcaacacgcttgtcatttacgtc
atcctccgctacgccaagatgaagacaatcaccaacatctacatcctcaacctggc-cattgccgat gagctcttcatgctgggcctgcccttcctggc-catgcaggtggctctggtccactggcccttttggc aaggccatctgccgggtggt-catgactgtggatggcatcaatcagttcaccagcattttctgcttg
accgtcatgagcattgaccggtacctggctgtggtccacccatcaagtcggc-caagtggaggaga ccccggacagccaagatgat-caatgtggccgtgtggggcgtctctctgctggtcatcttgcccatc atga-tatatgccgggcttcgaagcaaccagtggggagaagcagctgcaccatcaact ggccaggc gagtcgggggcatggtacacgggggttcattatctacgcctt-catcctgggggttcctggtgccctc accatcatctgtctttgctacctgttcattat-catcaaggtgaagtcctccggaatccgagtgggt tcctccaagaggaaaaagtct-gagaagaaggtcacccggatggtgtccattgtggtggccgtcttc
attttctgctggctcccccttctacatcttcaatgtctcttcggtctctgtggc-catcagtcccacc ccagcccttaaaggcatgtttgactttgtggtggtcctcacc-tatgctaacagctgtgccaaccct atcctctatgccttcttgtccgacaactt-caagaagagcttccagaatgtcctctgcttggtcaag
gtgagcggcacagatgatggggaacg-gagtgacagtaagcaggacaaatcgcggctgaatgagacc acgga-gacccagaggaccctcctcaatggagacctccagaccagtatctga Modified *Sus scrofa* SSTR2 Nucleotide Sequence (SEQ ID NO: 4)
atggatatggcgtatgagctactcacgggagccagccgtggctttcctctccat-tcgacctcaatg gctccgtggcaacagccaacagttcaaaccagacggagccat-actatgacctgaccagcaatgcag tcctcacgttcatatattttgtggtctgcatcat-tggcctgtgcggcaacacgcttgtcatttacg
tcatcctccgctacgccaagatgaagacaatcaccaacatctacatcct-caacctggccattgccg atgagctcttcatgctgggcctgcccttcctggc-catgcaggtggctctggtccactggccctttg gcaaggccatctgccgggtggt-catgactgtggatggcatcaatcagttcaccagcattttctgct tgaccgtcatgagcattgaccggtacctggctgtggtccacccca tcaagtcggc-caagtggagga gaccccggacagccaagatgat-caatgtggccgtgtggggcgtctctctgctggtcatcttgccca tcatga-tatatgccgggcttcgaagcaaccagtggggagaagcagctgcaccatcaact ggccag gcgagtcgggggcatggtacacgggggttcattatctacgcctt-catcctgggggttcctggtgccc ctcaccatcatctgtctttgctacctgttcattat-catcaaggtgaagtcctccggaatccgagtgg ttcctccaagaggaaaaagtct-gagaagaaggtcacccggatggtgtccattgtggtggccgtct
tcatttctgctggctcccccttctacatcttcaatgtctcttcggtctctgtggc-catcagtccca ccccagcccttaaaggcatgtttgactttgtggtggtcctcacc-tatgctaacagctgtgccaacc ctatcctctatgccttcttgtccgacaactt-caagaagagcttccagaatgtcctctgcttggtca
aggtgagcggcacagatgatggggaacggagtgacagtaagcaggacaaatcgcggctgaatgaga ccacggagacccagaggaccctcctcaatggagacctccagaccagtatctga
SSTR2 Guide RNA (SEQ ID NO: 5)
tggcgtatgagctactcaac Example 2

F₁ litters were generated by crossing the founder boar, 74-02, with three wild-type gilts. All of the piglets were heterozygous, carrying one wild type copy of the SSTR2 allele and one copy of either the 1 bp deletion (n=22) or 3 bp deletion (n=24) allele. All of the genotypes were confirmed with Sanger sequencing, and a subset were further verified by sequencing clones produced using TA cloning. Pigs were weaned at 21 days of age (1 bp deletion, n=16; 3 bp deletion, n=20) and were group housed with litter mates. After weaning, all pigs had ad libitum access to feed and water. Weights were recorded for each individual pig at birth and once every week through 49 days of age. Weights at each time point were analyzed using a mixed model in SAS 9.4 with dam as a random effect.

Figure 6:
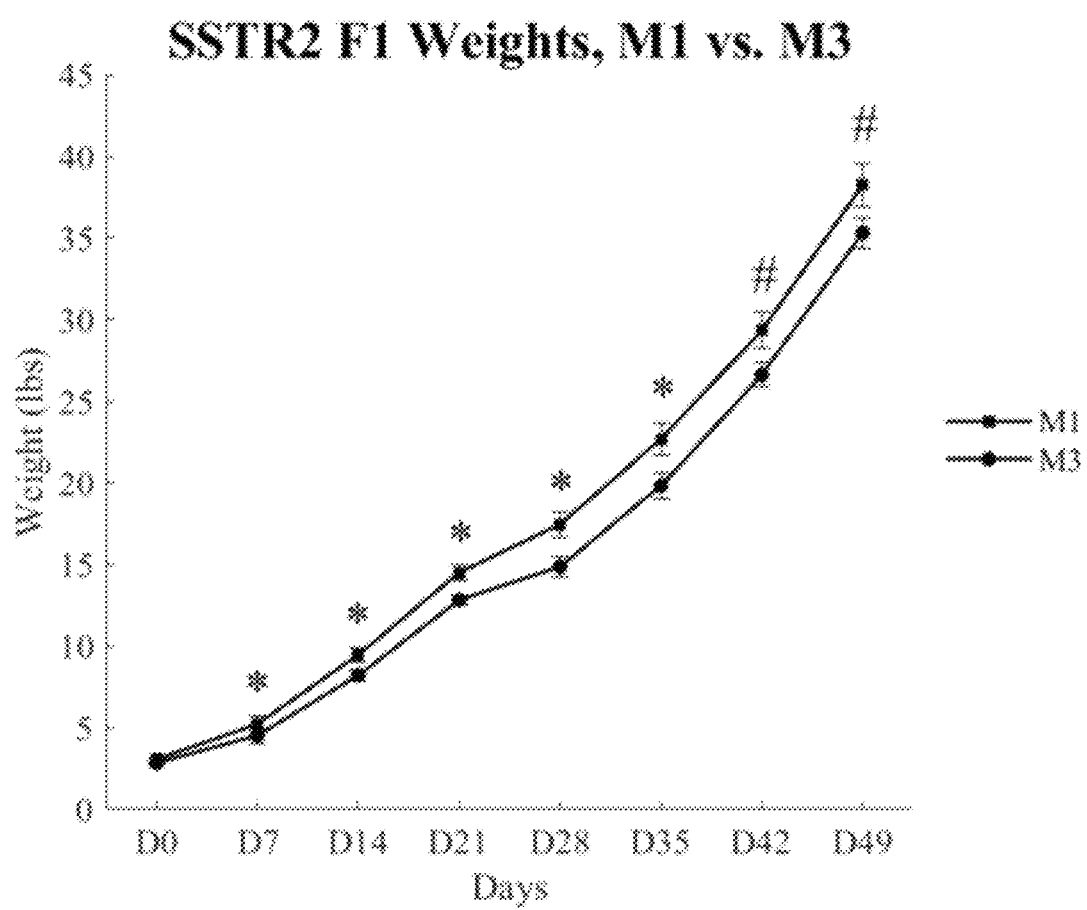
FIG. 6 shows weekly weight data comparing heterozygous males carrying the 1 bp deletion (n=6) and heterozygous males carrying the 3 bp deletion (n=12). No differences were observed between groups at birth, but differences were observed at all other time points (*, P<0.05; #, P<0.10).
Figure 7:
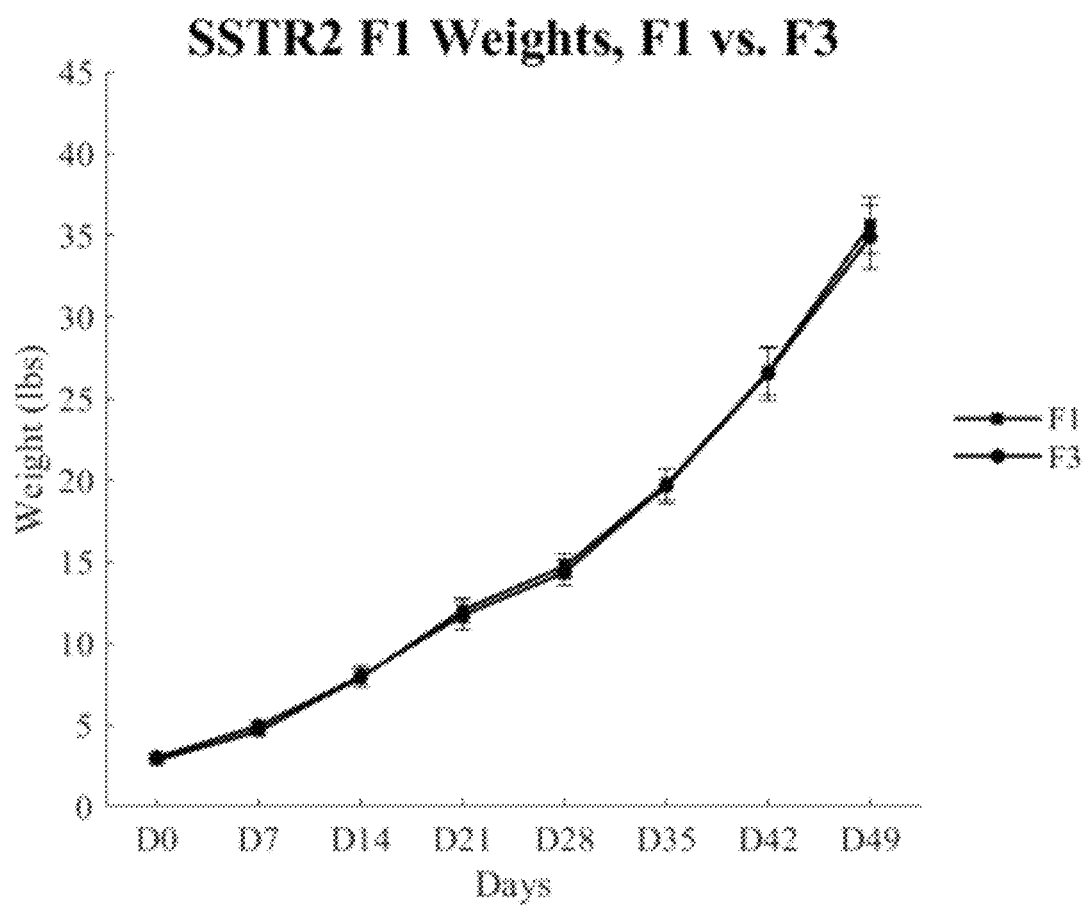
FIG. 7 shows weekly weight data comparing heterozygous females carrying the 1 bp deletion (n=10) and heterozygous females carrying the 3 bp deletion (n=8). No differences were observed between groups at any of the time points.

FIG. 6 shows weekly weight data comparing heterozygous males carrying the 1 bp deletion and heterozygous males carrying the 3 bp deletion. No differences were observed between groups at birth, but differences were observed at all other time points. FIG. 7 shows weekly weight data comparing heterozygous females carrying the 1 bp deletion and heterozygous females carrying the 3 bp deletion. No differences were observed between groups at any of the time points.

What is claimed is:

1. A genetically edited male or female pig, or progeny thereof, comprising an edited chromosomal sequence that reduces or eliminates expression or activity of a somatostatin receptor 2 (SSTR2) protein, wherein growth performance of the male pig comprising the edited chromosomal sequence is improved when compared to a non-edited male pig.

2. The genetically edited male or female pig of claim 1, wherein the edited chromosomal sequence comprises a substitution, insertion, or deletion of one or more nucleotides in the SSTR2 coding sequence.

3. The genetically edited male or female pig of claim 1, wherein the edited chromosomal sequence eliminates the expression or activity of the SSTR2 protein.

4. The genetically edited male or female pig of claim 1, wherein the edited chromosomal sequence comprises no exogenously introduced sequence.

5. The genetically edited male or female pig of claim 1, wherein the pig further comprises an edited chromosomal sequence that reduces or eliminates expression or activity of a SSTR1, SSTR3, SSTR4, or SSTR5 protein.

6. The genetically edited male or female pig of claim 1, wherein the pig is heterozygous or homozygous for the edited chromosomal sequence.

7. The genetically edited male or female pig of claim 1, wherein the pig is a male pig.

8. The genetically edited male or female pig of claim 1, wherein the edited chromosomal sequence comprises SEQ ID NO: 3 or 4.

9. A cell of the genetically edited male or female pig of claim 1.

10. The cell of claim 9, wherein the edited chromosomal sequence comprises a substitution, insertion, or deletion of one or more nucleotides in the SSTR2 coding sequence.

11. The cell of claim 9, wherein the cell further comprises an edited chromosomal sequence that reduces or eliminates expression or activity of a SSTR1, SSTR3, SSTR4, or SSTR5 protein.

12. The cell of claim 9, wherein the cell is heterozygous or homozygous for the edited chromosomal sequence.

13. The cell of claim 9, further comprising a conditional knock-out system for conditional expression of the SSTR2 protein.

14. The cell of claim 9, wherein the cell is a sperm cell or an egg cell.

15. The cell of claim 9, wherein the cell is a somatic cell.

16. The cell of claim 9, wherein the edited chromosomal sequence comprises SEQ ID NO: 3 or 4.

17. A method of generating a male or female pig comprising:
    editing a chromosomal sequence of the male or female pig to create a modification which reduces or eliminates the expression or activity of a somatostatin receptor 2 (SSTR2) protein, wherein growth performance of the male pig comprising the edited chromosomal sequence is improved.

18. The method of claim 17, wherein the editing is by use of a TALEN, a zinc finger nuclease, or a CRISPR system.

19. The method of claim 17, wherein the generating comprises use of somatic cell nuclear transfer.

20. The method of claim 17, wherein the edited chromosomal sequence comprises a substitution, insertion, or deletion of one or more nucleotides in the SSTR2 coding sequence.

* * * * *